US009315448B2

(12) United States Patent
Coppens

(10) Patent No.: US 9,315,448 B2
(45) Date of Patent: Apr. 19, 2016

(54) VIRAL INHIBITOR COMPOSITION FOR IN VIVO THERAPEUTIC USE

(75) Inventors: Christine Coppens, Strassen (LU); Willem Van Cauter, legal representative, Strassen (LU)

(73) Assignee: Cesa Alliance S.A., Luxembourg (LU)

( * ) Notice: Subject to any disclaimer, the term of this patent is extended or adjusted under 35 U.S.C. 154(b) by 227 days.

(21) Appl. No.: 14/008,092

(22) PCT Filed: Sep. 27, 2011

(86) PCT No.: PCT/EP2011/066746
§ 371 (c)(1),
(2), (4) Date: Dec. 5, 2013

(87) PCT Pub. No.: WO2012/038553
PCT Pub. Date: Mar. 29, 2012

(65) Prior Publication Data

US 2014/0088193 A1 Mar. 27, 2014

Related U.S. Application Data

(63) Continuation-in-part of application No. PCT/EP2011/054758, filed on Mar. 28, 2011.

(51) Int. Cl.

| | |
|---|---|
| ***A01N 37/10*** | (2006.01) |
| ***A61K 31/235*** | (2006.01) |
| ***A01N 35/00*** | (2006.01) |
| ***A61K 31/12*** | (2006.01) |
| ***C07C 69/88*** | (2006.01) |
| ***C07C 49/00*** | (2006.01) |
| ***C07C 69/84*** | (2006.01) |
| ***A61K 31/216*** | (2006.01) |
| ***A01N 35/04*** | (2006.01) |
| ***A01N 37/40*** | (2006.01) |
| ***C07C 49/248*** | (2006.01) |

(52) U.S. Cl.
CPC ................ *C07C 69/84* (2013.01); *A01N 35/04* (2013.01); *A01N 37/40* (2013.01); *A61K 31/12* (2013.01); *A61K 31/216* (2013.01); *A61K 31/235* (2013.01); *C07C 49/248* (2013.01)

(58) Field of Classification Search
CPC ...... C07C 69/84; C07C 49/248; A01N 35/04; A01N 37/40; A61K 2300/00; A61K 31/12; A61K 31/216; A61K 31/122; A61K 31/235; A61K 31/045; A61K 31/085; A61K 31/336; A61K 31/35
USPC ............ 514/475, 544, 689, 690, 729; 560/67; 568/337
See application file for complete search history.

(56) References Cited

PUBLICATIONS

International Committee on Taxonomy of Viruses, 2011 (http://talk.ictvonline.org/files/ictv_documents/m/msl/4090.aspx).*

* cited by examiner

*Primary Examiner* — Uma Ramachandran
(74) *Attorney, Agent, or Firm* — Fish & Tsang LLP

(57) ABSTRACT

The present invention concerns a pharmaceutical composition comprising a compound of formula A being (2,3(dihydroxy), 5[3(1,2)butadiene], 1(3hydroxy,3methyl,4pentene) benzene) and/or a compound of formula B being (2,3 (dihydroxy), 5[3(1,2)butadiene], 2[2methylbutane]benzenal) and/or a compound of formula C being (2,3(dihydroxy), 5[3 (1,2)butadiene], 2hydroxy,3butene benzoate) or a combination thereof for use as a medicament or for in vivo use in treatment and prevention of diseases caused by DNA enveloped viruses, DNA non-enveloped viruses, RNA enveloped viruses and RNA non-enveloped viruses.

18 Claims, No Drawings

VIRAL INHIBITOR COMPOSITION FOR IN VIVO THERAPEUTIC USE

FIELD OF THE INVENTION

The present invention relates to the pharmaceutical field. The man skilled in the art can be an organic chemist.

The present invention relates to a composition for use as a medicament according to claim 1, a composition for use in treatment and prevention of diseases caused by DNA enveloped, DNA non-enveloped, RNA enveloped, RNA non-enveloped viruses according to claim 2, use of the composition as a prophylactic according to claim 8, use of the composition as a disinfectant according to claim 11, use of the composition as a viral inhibitor according to claim 9 and claim 12.

BACKGROUND OF INVENTION

U.S. Pat. No. 4,402,950 discloses (in vitro) the antiviral activity of carvone against adenovirus type 6, which is a double stranded DNA non enveloped virus.

U.S. Pat. No. 4,402,950 discloses in its claim 1 "a process for deactivating viruses inside living human and animal organisms infected with said viruses comprising administering to one of said organisms a terpene selected from the group consisting of black pepper oil, cinnamon flower oil, cardamon oil, linallyl acetate, cinnamic aldehyde, carvone, and cis/trans citral, in a dosage amount effective to deactivate said viruses but ineffective to cause toxic effects on living cells of the living organism."

The difference between the present invention and U.S. Pat. No. 4,402,950 is a chemical structural difference. The prior art does not comprise any composition having a compound of formula A or B or C as defined in the claims of the present invention.

No prior art has been found having a compound of formula A or B or C as defined in the claims of the present invention.

The objective technical problem to be solved is considered as the provision of a novel composition having an antiviral effect.

There is no teaching in the prior art as a whole that would have prompted the skilled person, faced with the objective technical problem, to modify the closest prior art while taking account of that teaching, thereby arriving at something falling within the terms of the claims of the present invention and thus achieving what the invention achieves. The answer to this question is clearly NO.

GENERAL COMMENTS ON THE PRIOR ART DOCUMENTS

Any potential prior art document dealing with in vitro tests cannot be considered pertinent because the compositions of the present invention have been tested in vivo i.e. on animals and it is well known by a man skilled in the art that test results can strongly differ if they are performed in an in vitro versus an in vivo environment. An extensive literature search did not find out any evidence or correlation that even if a composition is active in vitro, a man skilled in the art could deduct that the same composition would also be active in vivo. We also refer to Antiviral research 42 (1999) pages 219-226 is entitled "plant products as topical microbicide candidates: assessment of in vitro and in vivo activity against herpes simplex virus type 2" where it is stated at page 224 first column "Several compounds showed activity in vitro but performed poorly in vivo. This failure of in vitro results to predict in vivo efficacy has previously been noted by zeitlin et al. (1997)".

SUMMARY OF THE INVENTION

The composition for use as a medicament is defined in claim 1 of the present invention, the composition for use in treatment and prevention of diseases caused by DNA enveloped, DNA non-enveloped, RNA enveloped, RNA non-enveloped viruses is defined in claim 2 of the present invention, the use of the composition as a prophylactic is defined in claim 8 of the present invention, the use of the composition as a disinfectant is defined in claim 11 of the present invention, the use of the composition as a viral inhibitor is defined in claim 9 and claim 12 of the present invention.

The technical effect of the present invention is to prevent viruses merging with the host cell(s) by interfering with the viral lipid envelope.

The technical problem to be solved is to prevent the multiplication of the viruses in animals and human beings and therefore curing diseased animals or human beings.

To solve the problem, the present invention provides a novel composition according to the claims.

It is inferred from some scientific studies that non-enveloped viruses acquire a lipid envelope from the host and as the composition of the present invention interferes with this triglyceride envelope and the envelope of enveloped viruses, it can be declared that the composition of the present invention will de-activate all types of viruses in vivo within animals or human beings.

Following are the most common viruses that can be deactivated with the compositions according to the present invention.

As the mode of action of the invention is non-specific, the virus species and serotype is irrelevant.

The person skilled in the virology field knows that all viruses are classified into 4 major groups consisting of DNA enveloped viruses, DNA non-enveloped viruses, RNA enveloped viruses and RNA non-enveloped viruses.

All compositions of the present invention are pharmaceutical compositions in a pharmaceutically effective weight percentage which can treat animal and/or human diseases.

List of Diseases: List E:

The compositions of the present invention are used for treating and preventing a disease related to one of the above mentioned viral groups as well as on diseases selected from the non exhaustive group consisting in: (broncho)-pneumonia, 3 day fever exanthema, acute and chronic hepatitis, acute fever, acute gastroenteritis caused by strains such as Desert Shield Lordsdale Mexico Norwalk Hawaii Snow Mountain Southampton virus, acute gastroenteritis caused by strains such as Houston/86 Houston/90 London 29845 Manchester Parkville Sapporo virus, acute hepatitis, acute respiratory distress syndrome, AIDS, anogenital mucosa, Argentine hemorrhagic fever, arthralgia, avian flu, Bolivian hemorrhagic fever, Brazilian hemorrhagic fever, chickenpox, chronic hepatitis, coma, common cold infection, common cold symptoms, congenital infection, conjunctivitis, contagious eethyma, contagious pustular dermatitis, cornea, cryptic enteric infection, cytomegaloviral mononucleosis, dengue hemorrhagic fever (DHF), dengue shock syndrome (DSS), diarrhea, eczema, eczema herpaticum, encephalitis, encephalopathy, enteritis, epidemic nephropathy, epidemic polyarthritis and exanthema, epidermodysplasia veruciformis, Epstein-Barr virus infection, exanthema, exanthema in children, Fatal familial insomnia, febrile encephalitis, febrile illness, fever, formerly Human echovirus 22 23, gastroenteritis, gastrointestinal infections intracytoplasmic inclusion bodies, genital tract infections, haemolytic crisis in people with sickle cell disease, headaches, hemorrhagic fever, hemorrhagic fever w renal syndrome, herpetic encephalitis, Hodgkin's disease, Human coxsackievirus, Human coxsackievirus B1-6, Human echovirus 1-7 9 11-21 24-27 29-33, Human enterovirus 69, Human enterovirus 71 (hand foot and mouth disease), Human hepatitis virus A (HHAV), Human poliovirus, Human rhinovirus 1 2 7 9 11 15 16 21 29 36 39 49 50 58 62 65 85 89 hyperacute respiratory disease, Human rhinovirus 3 14 72, hyperacute respiratory disease, immune deficiency syndrome, infantile diarrhea, Infection with any dengue serotype (1-4), infectious mononucleosis, joint pain, Kaposi's sarcoma, keratoconjunctivitis, lesions of coutanous sites, leucopoenia, liver cirrhosis, lower respiratory tract infection, lymphadenopathy, maculopapular rash, measles, meningitis, mononucleosis (kissing disease), mumps, muscle pains, myocarditis, nephropathy, nephropathy in transplant patients, numbness, old world, opportunistic infection, oral infections, oral mucosa, orchitis, pancreatitis, pandemics, papilloma, paralysis, persistent infection of the kidney, persistent infections, persistent lymphopathy, pharyngeal conjunctivitis, pneumonia, primary hepatocellular carcinoma, pulmonary syndrome, rabies, rash, recurrent epidemics of respiratory disease, respiratory disease, respiratory illness, Roseola infantum, sarcoma, scarring, sever chills arthralgia, severe acute respiratory syndrome, severe encephalitis, shingles, sixth disease, skin and mucous membrane lesions, slim disease, sore throat, subacute sclerosing panencephalitis, superinfection with Deltavirus, ulceration, upper respiratory tract illness, Venezuelan hemorrhagic fever, vesicular pharyngitis, vesicular stomatitis with exanthema, viral polyarthritis and rush, viral warts, watery diarrhea, weakness, zoonotic, zoster, metaplasia, dysplasia, anaplasia, desmoplasia, carcinoma in situ, flu (influenza), invasive carcinoma, as well as any disease directly or indirectly related to the above mentioned viruses.

Examples of Viruses:

Information about the viruses can be found on internet at the following link: http://www.ncbi.nlm.nih.gov/ICTVdb/Ictv/ICD-10.htm A non exhaustive list of viruses and their species which can be deactivated and therefore prevented from multiplication by the compositions of the present invention is as follows: Abadina virus (Reoviridae), Abelson murine leukemia virus (Retroviridae), Abras virus (Bunyaviridae), Absettarov virus (Flaviviridae), Abu Hammad virus (Bunyaviridae), Abu Mina virus (Bunyaviridae), Acado virus (Reoviridae), Acara virus (Bunyaviridae), Acciptrid herpesvirus (Herpesviridae), Acheta domestica densovirus (Parvoviridae), Acrobasis zelleri entomopoxvirus (Poxyiridae), Adelaide River virus (Rhabdoviridae), Adeno-associated virus (Parvoviridae), *Aedes aegypti* densovirus (Parvoviridae), *Aedes aegypti* entomopoxvirus (Poxyiridae), *Aedes albopictus* densovirus (Parvoviridae), *Aedes pseudoscutellaris* densovirus (Parvoviridae), African green monkey cytomegalovirus (Herpesviridae), African green monkey HHV-like virus (Herpesviridae), African green monkey polyomavirus (Papovaviridae), African horse sickness viruses (Reoviridae), African swine fever virus, African swine fever-like viruses, AG-virus (Bunyaviridae), AG-virus, (Bunyaviridae), *Agaricus bisporus* virus, Aguacate virus (Bunyaviridae), Ahlum water-borne virus (Tombusviridae), Aino virus (Bunyaviridae), Akabane virus (Bunyaviridae), AKR (endogenous) murine leukemia virus (Retroviridae), Alajuela virus (Bunyaviridae), Alcelaphine herpesvirus (Herpesviridae), Alenquer virus (Bunyaviridae), Aleutian disease virus (Parvoviridae), Aleutian mink disease virus (Parvoviridae), Alfuy virus (Flaviviridae), Allerton virus (Herpesviridae), Allitrich herpesvirus (Herpesviridae), Allomyces arbuscula virus, Almeirim virus (Reoviridae), Almpiwar virus (Rhabdoviridae), Altamira virus, (Reoviridae), Amapari virus (Arenaviridae), American ground squirrel herpesvirus, (Herpesviridae), Amsacta moorei entomopoxvirus (Poxyiridae), Amyelosis chronic stunt virus (Caliciviridae), Ananindeua virus (Bunyaviridae), Anatid herpesvirus (Herpesviridae), Andasibe virus (Reoviridae), Anhanga virus (Bunyaviridae), Anhembi virus (Bunyaviridae), *Anomala cuprea* entomopoxvirus (Poxyiridae), *Anopheles* A virus (Bunyaviridae), *Anopheles* virus (Bunyaviridae), Antequera virus (Bunyaviridae), Aotine herpesvirus (Herpesviridae), Apeu virus (Bunyaviridae), Aphodius tasmaniae entomopoxvirus (Poxyiridae), Apoi virus (Flaviviridae), Aransas Bay virus (Bunyaviridae), Arbia virus (Bunyaviridae), Arboledas virus (Bunyaviridae), Arbroath virus (Reoviridae), Argentine turtle herpesvirus (Herpesviridae), Arkonam virus (Reoviridae), Aroa virus (Flaviviridae), Arphia conspersa entomopoxvirus (Poxyiridae), Aruac virus (Rhabdoviridae), Arumowot virus (Bunyaviridae), Asinine herpesvirus (Herpesviridae), Atlantic cod ulcus syndrome virus (Rhabodoviridae), Atlantic salmon reovirus Australia (Reoviridae), Atlantic salmon reovirus Canada (Reoviridae), Atlantic salmon reovirus USA (Reoviridae), Atropa belladorma virus (Rhabdoviridae), Aucuba bacilliform virus, Badnavirus, Aujeszky's disease virus (Herpesviridae), Aura virus (Togaviridae), Auzduk disease virus (Poxyiridae), Avalon virus (Bunyaviridae), Avian adeno-associated virus (Parvoviridae), Avian carcinoma, Mill Hill virus (Retroviridae), Avian encephalomyelitis virus (Picornaviridae), Avian infectious bronchitis virus (Coronaviridae), Avian leukosis virus-RSA (Retroviridae), Avian myeloblastosis virus (Retroviridae), Avian myelocytomatosis virus (Retroviridae), Avian nephrites virus (Picornaviridae), Avian paramyxovirus (Paramyxoviridae), Avian reovirus (Reoviridae), B virus (Parvoviridae), B-lymphotropic papovavirus (Papovaviridae), Babahoya virus (Bunyaviridae), Babanki virus (Togaviridae), Baboon herpesvirus (Herpesviridae), Baboon polyomavirus (Papovaviridae), Bagaza virus (Flaviviridae), Bahia Grande virus (Rhabdoviridae), Bahig virus (Bunyaviridae), Bakau virus (Bunyaviridae), Baku virus (Reoviridae), Bald eagle herpesvirus (Herpesviridae), Bandia virus (Bunyaviridae), Bangoran virus (Rhabdoviridae), Bangui virus (Bunyaviridae), Banzi virus (Flaviviridae), Barmah Forest virus (Togaviridae), Barranqueras virus (Bunyaviridae), Barur virus (Rhabdoviridae), Batai virus (Bunyaviridae), Batarna virus (Bunyaviridae), Batken virus (Bunyaviridae), Bauline virus (Reoviridae), Beak and feather disease virus (Circoviridae), BeAn virus (Rhabdoviridae), BeAr virus (Bunyaviridae), Bebaru virus (Togaviridae), Belem virus (Bunyaviridae), Belmont virus ((Bunyaviridae)), Belterra virus (Bunyaviridae), Benevides virus (Bunyaviridae), Benfica virus (Bunyaviridae), Berne virus, (Coronaviridae), Berrimah virus (Rhabdoviridae), Bertioga virus (Bunyaviridae), Bhanja virus (Bunyaviridae), Bimbo virus (Rhabdoviridae), Bimiti virus (Bunyaviridae), Birao virus (Bunyaviridae), BivensArm virus (Rhabdoviridae), BK virus (Papovaviridae), Bluetongue viruses (Reoviridae), Bobaya virus (Bunyaviridae), Bobia virus (Bunyaviridae), Bobwhite quail herpesvirus (Herpesviridae), Boid herpesvirus (Herpesviridae), *Bombyx mori* densovirus (Parvoviridae), Boolarra virus (Nodaviridae), Boraceia virus (Bunyaviridae), Border disease virus (Flaviviridae), Boma disease virus, Botambi virus (Bunyaviridae), Boteke virus, (Rhabdoviridae), Bouboui virus (Flaviviridae), Bovine adeno-associated virus (Parvoviridae), Bovine adenoviruses (Adenoviridae), Bovine astrovirus (Astroviridae), Bovine coronavirus (Coronaviridae), Bovine diarrhea virus (Flaviviridae), Bovine encephalitis herpesvirus (Herpesviridae), Bovine enteric calicivirus (Caliciviridae), Bovine enterovirus (Picornaviridae), Bovine ephemeral fever virus (Rhabdoviridae), Bovine herpesvirus (Herpesviridae), Bovine immunodeficiency virus (Retroviridae), Bovine leukemia virus (Retroviridae), Bovine mamillitis virus (Herpesviridae), Bovine papillomavirus (Papovaviridae), Bovine papular stomatitis virus (Poxyiridae), Bovine parainfluenza virus (Paramyxoviridae), Bovine parvovirus (Parvoviridae), Bovine polyomavirus (Papovaviridae), Bovine respiratory syncytial virus (Paramyxoviridae), Bovine rhinovirus (Picornaviridae), Bovine syncytial virus (Retroviridae), Bozo virus (Bunyaviridae), Broadhaven virus (Reoviridae), Bruconha virus (Bunyaviridae), Brus Laguna virus (Bunyaviridae), Budgerigar fledgling disease virus (Papovaviridae), Buenaventura virus (Bunyaviridae), Buffalopox virus (Poxyiridae), Buggy Creek virus (Togaviridae), Bujaru virus (Bunyaviridae), Bukalasa bat virus (Flaviviridae), Bunyamwera virus (Bunyaviridae), Bunyip creek virus (Reoviridae), Bushbush virus (Bunyaviridae), Bussuquara virus (Flaviviridae), Bwamba virus (Bunyaviridae), Cache Valley virus (Bunyaviridae), Cacipacore virus (Flaviviridae), Caddo Canyon virus (Bunyaviridae), Caimito virus (Bunyaviridae), Calchaqui virus (Rhabdoviridae), California encephalitis virus (Bunyaviridae), California harbor sealpox virus (Poxyiridae), Callistephus chinensis chlorosis virus (Rhabdoviridae), Callitrichine herpesvirus (Herpesviridae), Camel contagious eethyma virus (Poxyiridae), Camelpox virus (Poxyiridae), Camptochironomus tentans entomopoxvirus (Poxyiridae), Cananeia virus (Bunyaviridae), Canarypox virus (Poxyiridae), Candiru virus (Bunyaviridae), Canid herpesvirus (Herpesviridae), Caninde virus (Reoviridae), Canine adeno-associated virus (Parvoviridae), Canine adenovirus (Adenoviridae), Canine calicivirus (Caliciviridae), Canine coronavirus (Coronaviridae), Canine distemper virus (Paramyxoviridae), Canine herpesvirus (Herpesviridae), Canine minute virus (Parvoviridae), Canine oral papillomavirus (Papovaviridae), Canine parvovirus (Parvoviridae), *Canna* yellow mottle virus (Badnavirus), Cape Wrath virus (Reoviridae), Capim virus (Bunyaviridae), Caprine adenovirus (Adenoviridae), Caprine arthritis encephalitis virus (Retroviridae), Caprine herpesvirus (Herpesviridae), Capuchin herpesvirus AL-(Herpesviridae), Capuchin herpesvirus AP-(Herpesviridae), Carajas virus (Rhabdoviridae), Caraparu virus (Bunyaviridae), Carey Island virus (Flaviviridae), Casphalia extranea densovirus (Parvoviridae), Catu virus (Bunyaviridae), Caviid herpesvirus ((Herpesviridae)), CbaAr virus (Bunyaviridae), Cebine herpesvirus (Herpesviridae), Cercopithecine herpesvirus (Herpesviridae), Cervid herpesvirus (Herpesviridae), CG-virus (Bunyaviridae), Chaco virus (Rhabdoviridae), Chagres virus (Bunyaviridae), Chamois contagious ecthvma virus (Poxyiridae), Chandipura virus (Rhabdoviridae), Changuinola virus (Reoviridae), Charleville virus (Rhabdoviridae), Chelonid herpesvirus (Herpesviridae), Chelonid herpesvirus (Herpesvirzdae), Chelonid herpesvirus (Herpesviridae), Chenuda virus (Reoviridae), Chick syncytial virus (Retroviridae), Chicken anemia virus (Circoviridae), Chicken parvovirus (Paruoviridae), Chikungunya virus (Togaviridae), Chilibre virus (Bunyaviridae), Chim virus (Bunyaviridae), Chimpanzee herpesvirus (Herpesviridae), *Chironomus attenuatus* entomopoxvirus (Poxyiridae), *Chironomus luridus* entomopoxvirus (Poxyiridae), *Chironomus plumosus* erltomopoxvirus (Poxyiridae), Chobar Gorge virus (Reoviridae), Choristoneura biennis entomopoxvirus (Poxyiridae), Choristoneura conflicta entomopoxvirus (Poxyiridae), Choristoneura diversuma entomopoxvirus (Poxyiridae), Chorizagrotis auxiliars entomopoxvirus (Poxyiridae), Chub reovirus Germany (Reoviridae), Ciconiid herpesvirus (Herpesviridae), Clo Mor virus (Bunyaviridae), CoAr-virus (Bunyaviridae), Coastal Plains virus (Rhabdoviridae), Cocal virus (Rhabdoviridae), Coital exanthema virus (Herpesviridae), ColAn-virus (Bunyaviridae), Colocasia bobone disease virus, (Rhabdoviridae), Colorado tick fever virus, (Reoviridae), Columbia SK virus, (Picornaviridae), Columbid herpesvirus, (Herpesviridae), Connecticut virus, (Rhabdoviridae), Contagious eethyma virus, (Poxyiridae), Contagious pustular dermatitis virus, (Poxyiridae), Corfu virus, (Bunyaviridae), Corriparta virus, (Reoviridae), Cotia virus, (Poxyiridae), Cowpox virus, (Poxyiridae), Crimean-Congo hemorrhagic fever virus, (Bunyaviridae), CSIRO village virus, (Reoviridae), Cynara virus, (Rhabdoviridae), Cyprinid herpesvirus, (Herpesviridae), Dabakala virus, (Bunyaviridae), D'Aguilar virus, (Reoviridae), Dakar bat virus, (Flaviviridae), DakArk virus, (Rhabdoviridae), Deer papillomavirus, (Papovaviridae), Demodema boranensis entomopoxvirus, (Poxyiridae), Dengue virus, (Flaviviridae), Dengue virus group, (Flaviviridae), Dependovirus, (Parvoviridae), Dera Ghazi Khan virus, (Bunyaviridae), Dera Ghazi Khan virus Group, (Bunyaviridae), Dermolepida albohirtum entomopoxvirus, (Poxyiridae), Dhori virus, (Orthomyxoviridae), *Diatraea saccharalis* densovirus, (Parvoviridae), Dobrava-Belgrade virus, (Bunyaviridae), Dolphin distemper virus, (Paramyxoviridae), Dolphinpox virus, (Poxyiridae), Douglas virus, (Bunyaviridae), *Drosophila* C virus, (Picornaviridae), Dry Tortugas virus, (Bunyaviridae), duck adenovirus, (Adenoviridae), Duck adenovirus, (Adenoviridae), Duck astrovirus, (Astroviridae), Duck hepatitis B virus, (Hepadnaviridae), Duck plague herpesvirus syn. anatid herpesvirus, (Herpesviridae), Dugbe virus, (Bunyaviridae), Duvenhage virus, (Rhabdoviridae), Eastern equine encephalitis virus, (Togaviridae), Ebola virus Filoviridae, *Echinochloa* hoja blanca virus; Genus *Tenuivirus, Echinochloa* ragged stunt virus, (Reoviridae), ectromelia virus, (Poxyiridae), Edge Hill virus, (Flaviviridae), Egtved virus syn. viral hemorrhagic septicemia virus, (Rhabdoviridae), Elapid herpesvirus, (Herpesviridae), Elephant loxondontal herpesvirus, (Herpesviridae), Elephant papillomavirus, (Papovaviridae), Elephantid herpesvirus, (Herpesviridae), Ellidaey virus, (Reoviridae), Embu virus, (Poxyiridae), Encephalomyocarditis virus, (Picornaviridae), Enseada virus, (Bunyaviridae), Entamoeba virus, (Rhabdoviridae), Entebbe bat virus, (Flaviviridae), Epizootic hemorrhagic disease viruses, (Reoviridae), Epstein-Barr virus, (Herpesviridae), Equid herpesvirus, (Herpesviridae), Equid herpesvirus, (Nerpesviridae), Equid herpesvirus, (Herpesviridae), Equine abortion herpesvirus, (Herpesviridae), Equine adeno-associated virus, (Parvoviridae), Equine adenovirus, (Adenoviridae), Equine arteritis virus, (Arterivirus), Equine cytomegalovirus, (Herpesviridae), Equine encephalosis viruses, (Reoviridae), Equine herpesvirus, (Herpesviridae), Equine infectious anemia virus, (Retroviridae), Equine papillomavirus, (Papovaviridae), Equine rhinopneumonitis virus, (Herpesviridae), Equine rhinovirus, (Picornaviridae), Eret-virus, (Bunyaviridae), Erinaceid herpesvirus, (Herpesviridae), Erve virus, (Bunyaviridae), Erysimum latent virus, Tymovirus, Esocid herpesvirus, (Herpesviridae), Essaouira virus, (Reoviridae), Estero Real virus, (Bunyaviridae), Eubenangee virus, (Reoviridae), Euonymus fasciation virus, (Rhabdoviridae), European bat virus, (Rhabdoviridae), European brown hare syndrome virus, (Caliciviridae), European elk papillomavirus, (Papovaviridae), European ground squirrel cytomegalovirus, (Herpesviridae), European hedgehog herpesvirus, (Herpesviridae), Everglades virus, (Togaviridae), Eyach virus, (Reoviridae), Facey's Paddock virus, (Bunyaviridae), Falcon inclusion body disease, (Herpesviridae), Falconid herpesvirus, (Herpesviridae), Farallon virus, (Bunyaviridae), Felid herpesvirus, (Herpesviridae), Feline calicivirus, (Caliciviridae), Feline herpesvirus, (Herpesviridae), Feline immunodeficiency virus, (Retroviridae), Feline infectious peritonitis virus, (Coronaviridae), Feline leukemia virus, (Retroviridae), Feline parlleukopenia virus, (Parvoviridae), Feline parvovirus, (Parvoviridae), Feline syncytial virus, (Retroviridae), Feline viral rhinotracheitis virus, (Herpesviridae), Fetal rhesus kidney virus, (Papovaviridae), Field mouse herpesvirus, (Herpesviridae), Figulus subleavis entomopoxvirus, (Poxyiridae), Fiji disease virus, (Reoviridae), Fin V-virus, (Bunyaviridae), Finkel-Biskis-Jinkins murine sarcoma virus, (Retroviridae), Flanders virus, (Rhabdoviridae), Flexal virus, (Arenaviridae), Flock house virus, Nodaviridae, Foot-and-mouth disease virus A, (Picornaviridae), Foot-and-mouth disease virus ASIA, (Picornaviridae), Foot-and-mouth disease virus, (Picornaviridae), Forecariah virus, (Bunyaviridae), Fort Morgan virus, (Togaviridae), Fort Sherman virus, (Bunyaviridae), Foula virus, (Reoviridae), Fowl adenoviruses, (Adenoviridae), Fowl calicivirus, (Caliciviridae), Fowlpox virus, (Poxyiridae), Fraser Point virus, (Bunyaviridae), Friend murine leukemia virus, (Retroviridae), Frijoles virus, (Bunyaviridae), Frog herpesvirus, (Herpesviridae), Fromede virus, (Reoviridae), Fujinami sarcoma virus, (Retroviridae), Fukuoka virus, (Rhabdoviridae), Gabek Forest virus, (Bunyaviridae), Gadget's Gully virus, (Flaviviridae), *Galleria mellonella* densovirus, (Parvoviridae), Gallid herpesvirus, (Herpesviridae), Gamboa virus, (Bunyaviridae), Gan Gan virus, (Bunyaviridae), Garba virus, (Rhabdoviridae), Gardner-Arnstein feline sarcoma virus, (Retroviridae), Geochelone carbonaria herpesvirus, (Herpesviridae), Geochelone chilensis herpesvirus, (Herpesviridae), Geotrupes sylvaticus entomopoxvirus, (Poxyiridae), Gerbera symptomless virus, (Rhabdoviridae), Germiston virus, (Bunyaviridae), Getah virus, (Togaviridae), Gibbon ape leukemia virus, (Retroviridae), Ginger chlorotic fleckvirus, Sobemovirus, Glycine mottle virus, Tombusviridae, Goat herpesvirus, (Herpesviridae), Goatpox virus, (Poxyiridae), Goeldichironomus holoprasimus entomopoxvirus, (Poxyiridae), Golden shiner reovirus, (Reoviridae), Gomoka virus, (Reoviridae), Gomphrena virus, (Rhabdoviridae), Gonometa virus, (Picornaviridae), Goose adenoviruses, (Adenoviridae), Goose parvovirus, (Parvoviridae), Gordil virus, (Bunyaviridae), Gorilla herpesvirus, (Herpesviridae), Gossas virus, (Rhabdoviridae), Grand Arbaud virus, (Bunyaviridae), Gray Lodge virus, (Rhabdoviridae), Gray patch disease agent of green sea turtle, (Herpesviridae), Great Island virus, (Reoviridae), Great Saltee Island virus, (Reoviridae), Great Saltee virus, (Bunyaviridae), Green iguana herpesvirus, (Herpesviridae), Green lizard herpesvirus, (Herpesviridae), Grey kangaroopox virus, (Poxyiridae), Grimsey virus, (Reoviridae), Ground squirrel hepatitis B virus, (Hepadnaviridae), GroupA-K rotaviruses, (Reoviridae), Gruid herpesvirus, (Herpesviridae), GUU-virus, (Bunyaviridae), Guajara virus, (Bunyaviridae), Guama virus, (Bunyaviridae), Guanarito virus, (Arenaviridae), Guaratuba virus, (Bunyaviridae), Guaroa virus, (Bunyaviridae), Guinea pig cytomegalovirus, (Herpesviridae), Guinea pig herpesvirus, (Herpesviridae), Guinea pig type C oncovirus, (Retroviridae), Gumbo Limbo virus, (Bunyaviridae), Gurupi virus, (Reoviridae), H-virus, (Parvoviridae), H virus, (Bunyaviridae), Hamster herpesvirus, (Herpesviridae), Hamster polyomavirus, (Papovaviridae), Hantaan virus, (Bunyaviridae), Hanzalova virus, (Flaviviridae), Hardy-Zuckerman feline sarcoma virus, (Retroviridae), Hare fibroma virus, (Poxyiridae), Hart Park virus, (Rhabdoviridae), Hartebeest herpesvirus, (Herpesviridae), Harvey murine sarcoma virus, (Retroviridae), Hazara virus, (Bunyaviridae), HB virus, (Parvoviridae), Hepatitis virus, (Picornaviridae), Hepatitis virus, (Hepadnaviridae), Hepatitis virus, (Flaviviridae), Herpesvirus M, (Herpesviridae), Herpesvirus papio, (Herpesviridae), Herpesvirus platyrrhinae type, (Herpesviridae), Herpesvirus pottos, (Herpesviridae), Herpesvirus saimiri, (Herpesviridae), Herpesvirus salmonis, (Herpesviridae), Herpesvirus sanguinus, (Herpesviridae), Herpesvirus scophthalmus, (Herpesviridae), Herpesvirus sylvilagus, (Herpesviridae), Herpesvirus T, (Herpesviridae), Herpesvirus tarnarinus, (Herpesviridae), Highlands J virus, (Togaviridae), Hirame rhabdovirus, (Rhabdoviridae), Hog cholera virus, (Flaviviridae), HoJo virus, (Bunyaviridae), Hepatitis delta virus, Satellites, Deltavirus, Hsiung Kaplow herpesvirus, (Herpesviridae), Hepatitis E virus, (Caliciviridae), Hepatopancreatic parvo-like virus of shrimps, (Parvoviridae), Heron hepatitis B virus, (Hepadnaviridae), Herpes ateles, (Herpesviridae), Herpes simiae virus, (Herpesviridae), Herpes simplex virus, (Herpesviridae), Herpes virus B, (Herpesviridae), Herpesvirus aotus, (Herpesviridae), Herpesvirus ateles strain, (Herpesviridae), Herpesvirus cuniculi, (Herpesviridae), Herpesvirus cyclopsis, (Herpesviridae), Huacho virus, (Reoviridae), Hughes virus, (Bunyaviridae), Human adenoviruses, (Adenoviridae), Human astrovirus, (Astroviridae), Human calicivirus, (Caliciviridae), Human caliciviruses, (Caliciviridae), Human coronavirus E, (Coronaviridae), Human coronavirus OC, (Coronaviridae), Human coxsackievirus, (Picornaviridae), Human cytomegalovirus, (Herpesviridae), Human echovirus, (Picornaviridae), Human enterovirus, (Picornaviridae), Human foamy virus, (Retroviridae), Human herpesvirus, (Herpesviridae), Human herpesvirus, Nerpesviridae, Human herpesvirus, (Herpesviridae), Human immunodeficiency virus, (Retroviridae), Human papillomavirus, (Papovaviridae), Human parainfluenza virus, (Paramyxoviridae), Human poliovirus, (Picornaviridae), Human respiratory syncytial virus, (Paramyxoviridae), Human rhinovirus, (Picornaviridae), Human spumavirus, (Retroviridae), Human T-lymphotropic virus, (Retroviridae), Humpty Doo virus, (Rhabdoviridae), HV-virus, (Bunyaviridae), Hypr virus, (Flaviviridae), Laco virus, (Bunyaviridae), Ibaraki virus, (Reoviridae), Icoaraci virus, (Bunyaviridae), Ictalurid herpesvirus, (Herpesviridae), Leri virus, (Reoviridae), Ife virus, (Reoviridae), Iguanid herpesvirus, (Herpesviridae), Ilesha virus, (Bunyaviridae), Ilheus virus, (Flaviviridae), Inclusion body rhinitis virus, (Herpesviridae), Infectious bovine rhinotracheitis virus, (Herpesviridae), Infectious bursal disease virus, Birnaviridae, Infectious hematopoietic necrosis virus, (Rhabdoviridae), Infectious laryngotracheitis virus, (Herpesviridae), Infectious pancreatic necrosis virus, Birnavirzdae, InfluenzaA virus (A/PR// (HN), (Orthomyxoviridae), Influenza B virus (B/Lee/), (Orthomyxoviridae), Influenza C virus (C/California/), (Orthomyxoviridae), Ingwavuma virus, (Bunyaviridae), Inini virus, (Bunyaviridae), Inkoo virus, (Bunyaviridae), Inner Farne virus, (Reoviridae), Ippy virus, (Arenaviridae), Irituia virus, (Reoviridae), Isfahan virus, (Rhabdoviridae), Israel turkey meningoencephalitis virus, (Flaviviridae), Issyk-Kul virus, (Bunyaviridae), Itaituba virus, (Bunyaviridae), Itaporanga virus, (Bunyaviridae), Itaqui virus, (Bunyaviridae), Itimirirn virus, (Bunyaviridae), Itupiranga virus, (Reoviridae), Jaagsiekte virus, (Retroviridae), Jacareacanga virus, (Reoviridae), Jamanxi virus, (Reoviridae), Jamestown Canyon virus, (Bunyaviridae), Japanaut virus, (Reoviridae), Japanese encephalitis virus, (Flaviviridae), Jari virus, (Reoviridae), JC virus, (Papovaviridae), Joa virus, (Bunyaviridae), Joinjakaka virus, (Rhabdoviridae), Juan Diaz virus, (Bunyaviridae), Jugra virus, (Flaviviridae), Juncopox virus, (Poxyiridae), Junin virus, (Arenaviridae), Junonia coenia densovirus, (Parvoviridae), Jurona virus, (Rhabdoviridae), Jutiapa virus, (Flaviviridae), K virus, (Papovaviridae), K virus, (Bunyaviridae), Kachemak Bay virus, (Bunyaviridae), Kadarn virus, (Flaviviridae), Kaeng Khoi virus, (Bunyaviridae), Kaikalur virus, (Bunyaviridae), Kairi virus, (Bunyaviridae), Kaisodi virus, (Bunyaviridae), Kala Iris virus, (Reoviridae), Kamese virus, (Rhabdoviridae), Karnmavanpettai virus, (Reoviridae), Kannamangalam virus, (Rhabdoviridae), Kao Shuan virus, (Bunyaviridae), Karimabad virus, (Bunyaviridae), Karshi virus, (Flaviviridae), Kasba virus, (Reoviridae), Kasokero virus, (Bunyaviridae), Kedougou virus, (Flaviviridae), Kemerovo virus, (Reoviridae), Kenai virus, (Reoviridae), Kennedya virus Y, Potyviridae, Kern Canyon Yirus, (Rhabdoviridae), Ketapang virus, (Bunyaviridae), Keterah virus, (Bunyaviridae), Keuraliba virus, (Rhabdoviridae), Keystone virus, (Bunyaviridae), Kharagysh virus, (Reoviridae), Khasan virus, (Bunyaviridae), Kilham rat virus, (Parvoviridae), Kimberley virus, (Rhabdoviridae), Kindia virus, (Reoviridae), Kinkajou herpesvirus, (Herpesviridae), Kirsten murine sarcoma yirus, (Retroviridae), Kismayo virus, (Bunyaviridae), Klamath virus, (Rhabdoviridae), Kokobera virus, (Flaviviridae), Kolongo virus, (Rhabdoviridae), Koolpinyah virus, (Rhabdoviridae), Koongol virus, (Bunyaviridae), Kotonkan virus, (Rhabdoviridae), Koutango virus, (Flaviviridae), Kowanyama virus, (Bunyaviridae), Kumlinge virus, (Flaviviridae), Kunjin virus, (Flaviviridae), Kwatta virus, (Rhabdoviridae), Kyzylagach virus, (Togaviridae), La Crosse virus, (Bunyaviridae), La Joya virus, (Rhabdoviridae), La-Piedad-Michoacan-Mexico virus, (Paramyxoviridae), Lacertid herpesvirus, (Herpesviridae), Lactate dehydrogenase-elevating virus, (Arterivirus), Lagos bat virus, (Rhabdoviridae), Lake Clarendon virus, (Reoviridae), Lake Victoria cormorant herpesvirus, (Herpesviridae), Langat virus, Ftaviviridae, Langur virus, (Retroviridae), Lanjan virus, (Bunyaviridae), Lapine parvovirus, (Parvoviridae), Las Maloyas virus, (Bunyaviridae), Lassa virus, (Arenaviridae), Lato river virus, (Tombusviridae), Le Dantec virus, (Rhabdoviridae), Leanyer virus, (Bunyaviridae), Lebombo virus, (Reoviridae), Lednice virus, (Bunyaviridae), Lee virus, (Bunyaviridae), Leporid herpesvirus, (Herpesviridae), Leucorrhinia dubia densovirus, (Parvoviridae), Lipovnik virus, (Reoviridae), Liverpool vervet monkey virus, (Herpesviridae), Llano Seco virus, (Reoviridae), *Locusta migratona* entomopoxvirus, (Poxyiridae), Lokem virus, (Bunyaviridae), Lone Star virus, (Bunyaviridae), Lorisine herpesvirus, (Herpesviridae), Louping ill virus, Flauiviridae, Lucke frog herpesvirus, (Herpesviridae), Lum virus, (Parvoviridae), Lukuni virus, (Bunyaviridae), Lumpy skin disease virus, (Poxyiridae), Lundy virus, (Reoviridae), *Lymantria dubia* densovirus, (Parvoviridae), Lymphocytic choriomeningitis virus, (Arenaviridae), Machupo virus, (Arenaviridae), Macropodid herpesvirus (Herpesviridae), Madrid virus, (Bunyaviridae), Maguari virus, (Bunyaviridae), Main Drain virus, (Bunyaviridae), Malakal virus, (Rhabdoviridae), Malignant catarrhal fever virus of European cattle, (Herpesviridae), Malpais Spring virus, (Rhabdoviridae), Malva silvestris virus, (Rhabdoviridae), Manawa virus, (Bunyaviridae), Manawatu virus, (Nodaviridae), Manitoba virus, (Rhabdoviridae), Manzanilla virus, (Bunyaviridae), Map turtle herpesvirus, (Herpesviridae), Mapputta virus, (Bunyaviridae), Maprik virus, (Bunyaviridae), Maraba virus, (Rhabdoviridae), Marburg virus, (Filoviridae), Marco virus, (Rhabdoviridae), Marek's disease herpesvirus, (Herpesviridae), Marituba virus, (Bunyaviridae), Marmodid herpesvirus, (Herpesviridae), Marmoset cytomegalovirus, (Herpesviridae), Marmoset herpesvirus, (Herpesviridae), Marmosetpox virus, (Poxyiridae), Marrakai virus, (Reoviridae), Mason-Pfizer monkey virus, (Retroviridae), Masou salmon reovirus, (Reoviridae), Matruh virus, (Bunyaviridae), Matucare virus, (Reoviridae), Mayaro virus, (Togaviridae), Mboke virus, (Bunyaviridae), Meaban virus, (Flaviviridae), Measles (Edmonston) virus, (Paramyxoviridae), Medical Lake macaque herpesvirus, (Herpesviridae), *Melanoplus sanguinipes* entomopoxvirus, (Poxyiridae), Melao virus, (Bunyaviridae), Meleagrid herpesvirus, (Herpesviridae), Melilotus latent virus, (Rhabdoviridae), Melolontha melolontha entomopoxvirus, (Poxyiridae), Mengovirus, (Picornaviridae), Mermet virus, (Bunyaviridae), Mice minute virus, (Parvoviridae), Mice pneumotropic virus, (Papovaviridae), Microtus pennsylvanicus herpesvirus, (Herpesviridae), Middelburg virus, (Togaviridae), Miller's nodule virus, (Poxyiridae), Mill Door virus, (Reoviridae), Minatitlan virus, (Bunyaviridae), Mink calicivirus, (Caliciviridae), Mink enteritis virus, (Parvoviridae), Minnal virus, (Reoviridae), Mirabilis mosaic virus, Caulimovirus, Mirim virus, (Bunyaviridae), Mitchell river virus, (Reoviridae), Mobala virus, (Arenaviridae), Modoc virus, (Flaviviridae), Moju virus, (Bunyaviridae), Mojui dos Campos virus, (Bunyaviridae), Mokola virus, (Rhabdoviridae), Molluscum contagiosum virus, (Poxyiridae), Molluscum-likepox virus, (Poxyiridae), Moloney murine sarcoma virus, (Retroviridae), Moloney virus, (Retroviridae), Monkey pox virus, (Poxyiridae), Mono Lake virus, (Reoviridae), Montana myotis leukoencephalitis virus, (Flaviviridae), Monte Dourado virus, (Reoviridae), Mopeia virus, (Arenaviridae), Moriche virus, (Bunyaviridae), Mosqueiro virus, (Rhabdoviridae), Mossuril virus, (Rhabdoviridae), Mount Elgon bat virus, (Rhabdoviridae), Mouse cytomegalovirus, (Herpesviridae), Mouse Elberfield virus, (Picornaviridae), Mouse herpesvirus strain, (Herpesviridae), Mouse mammary tumor virus, (Retroviridae), Mouse thymic herpesvirus, (Herpesviridae), Movar herpesvirus, (Herpesviridae), Mucambo virus, (Togaviridae), Mudjinbarry virus, (Reoviridae), Muir Springs virus, (Rhabdoviridae), Mule deerpox virus, (Poxyiridae), Multimammate mouse papillomavirus, (Papovaviridae), Mumps virus, (Paramyxoviridae), Murid herpesvirus, (Herpesviridae), Murine adenovirus, (Adenoviridae), Z murine adenovirus, (Adenoviridae), Murine hepatitis virus, (Coronaviridae), Murine herpesvirus, (Herpesviridae), Murine leukemia virus, (Retroviridae), Murine parainfluenza virus, (Paramyxoviridae), Murine poliovirus, (Picornaviridae), Murine polyomavirus, (Papovaviridae), Murray Valley encephalitis virus, (Flaviviridae), Murre virus, (Bunyaviridae), Murutucu virus, (Bunyaviridae), Mykines virus, (Reoviridae), Mynahpox virus, (Poxyiridae), Myxoma virus, (Poxyiridae), Nairobi sheep disease virus, (Bunyaviridae), Naranjal virus, (Flaviviridae), Nasoule virus, (Rhabdoviridae), Navarro virus, (Rhabdoviridae), Ndelle virus, (Reoviridae), Ndumu virus, (Togaviridae), Neckar river virus, (Tombusviridae), Negishi virus, (Flaviviridae), Nelson Bay virus, New Minto virus, (Rhabdoviridae), Newcastle disease virus, (Paramyxoviridae), Ngaingan virus, (Rhabdoviridae), Ngari virus, (Bunyaviridae), Ngoupe virus, (Reoviridae), Nile crocodilepox virus, (Poxyiridae), Nique virus, (Bunyaviridae), Nkolbisson virus, (Rhabdoviridae), Nola virus, (Bunyaviridae), North Clett virus, (Reoviridae), North End virus, (Reoviridae), Northern cereal mosaic virus, (Rhabdoviridae), Northern pike herpesvirus, (Herpesviridae), Northway virus, (Bunyaviridae), NorwaLk virus, (Caliciviridae), Ntaya virus, (Flaviviridae), Nugget virus, (Reoviridae), Nyabira virus, (Reoviridae), Nyamanini virus, Unassigned, Nyando virus, (Bunyaviridae), Oak-Vale virus, (Rhabdoviridae), Obodhiang virus, (Rhabdoviridae), Oceanside virus, (Bunyaviridae), Ockelbo virus, (Togaviridae), Odrenisrou virus, (Bunyaviridae), Oedaleus senegalensis entomopoxvirus, (Poxyiridae), Oita virus, (Rhabdoviridae), Okhotskiy virus, (Reoviridae), Okola virus, (Bunyaviridae), Olifantsvlei virus, (Bunyaviridae), Omo virus, (Bunyaviridae), Omsk hemorrhagic fever virus, (Flaviviridae), Onchorhynchus masou herpesvirus, (Herpesviridae), O'nyong-nyong virus, (Togaviridae), *Operophtera brurnata* entomopoxvirus, (Poxyiridae), Orangutan herpesvirus, (Herpesviridae), Orf virus, (Poxyiridae), Oriboca virus, (Bunyaviridae), Oriximina virus, (Bunyaviridae), Oropouche virus, (Bunyaviridae), Orungo virus, (Reoviridae), Oryctes rhinoceros virus, Unassigned, Ossa virus, (Bunyaviridae), Ouango virus, (Rhabdoviridae), Oubi virus, (Bunyaviridae), Ourem virus, (Reoviridae), Ovine adeno-associated virus, (Parvoviridae), Ovine adenoviruses, (Adenoviridae), (Astroviridae), Ovine herpesvirus, (Herpesviridae), Ovine pulrnonary adenocarcinoma virus, (Retroviridae), Owl hepatosplenitis herpesvirus, (Herpesviridae), P virus, (Bunyaviridae), Pacheco's disease virus, (Herpesviridae), Pacora virus, (Bunyaviridae), Pacui virus, (Bunyaviridae), Pahayokee virus, (Bunyaviridae), Palestina virus, (Bunyaviridae), Palyam virus, (Reoviridae), Pan herpesvirus, (Herpesviridae), Papio Epstein-Barr herpesvirus, (Herpesviridae), Para virus, (Bunyaviridae), Pararnushir virus, (Bunyaviridae), Parana virus, (Arenaviridae), Parapoxvirus of red deer in New Zealand, (Poxyiridae), Paravaccinia virus, (Poxyiridae), Parma wallaby herpesvirus, (Herpesviridae), Paroo river virus, (Reoviridae), Parrot herpesvirus, (Herpesviridae), Parry Creek virus, (Rhabdoviridae), Pata virus, (Reoviridae), Patas monkey herpesvirus pH delta, (Herpesviridae), Pathum Thani virus, (Bunyaviridae), Patois virus, (Bunyaviridae), Peaton virus, (Bunyaviridae), Percid herpesvirus, (Herpesviridae), Perdicid herpesvirus, (Herpesviridae), Perinet virus, (Rhabdoviridae), Periplanata fuliginosa densovirus, (Parvoviridae), Peste-des-petits-ruminants virus, (Paramyxoviridae), Petevo virus, (Reoviridae), Phalacrocoracid herpesvirus, (Herpesviridae), Pheasant adenovirus, (Adenoviridae), Phnom-Penh bat virus, (Flaviviridae), Phocid herpesvirus, (Herpesviridae), Phocine (seal) distemper virus, (Paramyxoviridae), Pichinde virus, (Arenaviridae), Picola virus, (Reoviridae), *Pieris rapae* densovirus, (Parvoviridae), Pigeon herpesvirus, (Herpesviridae), Pigeonpox virus, (Poxyiridae), Badnavirus Piry virus, (Rhabdoviridae), *Pisum* virus, (Rhabdoviridae), Pixuna virus, (Togaviridae), Playas virus, (Bunyaviridae), Pleuronectid herpesvirus, (Nerpesviridae), Pneumonia virus of mice, (Paramyxoviridae), Pongine herpesvirus, (Herpesviridae), Pongola virus, (Bunyaviridae), Ponteves virus, (Bunyaviridae), Poovoot virus, (Reoviridae), Porcine adenoviruses, (Adenoviridae), Porcine astrovirus, (Astroviridae), Porcine circovirus, Circoviridae, Porcine enteric calicivirus, (Caliciviridae), Porcine enterovirus, (Picornaviridae), Porcine epidemic diarrhea virus, (Coronaviridae), Porcine hemagglutinating encephalomyelitis virus, (Coronaviridae), Porcine parvovirus, (Parvoviridae), Porcine respiratory and reproductive syndrome, (Arterivirus), Porcine rubulavirus, (Paramyxoviridae), Porcine transmissible gastroenteritis virus, (Coronaviridae), Porcine type C oncovirus, (Retroviridae), Porton virus, (Rhabdoviridae), Potosi virus, (Bunyaviridae), Powassan virus, (Flaviviridae), Precarious Point virus, (Bunyaviridae), Pretoria virus, (Bunyaviridae), Primate calicivirus, (Caliciviridae), Prospect Hill virus, (Bunyaviridae), *Pseudaletia* includens densovirus, (Parvoviridae), Pseudocowpox virus, (Poxyiridae), Pseudolumpy skin disease virus, (Herpesviridae), Pseudorabies virus, (Herpesviridae), Psittacid herpesvirus, (Herpesviridae), Psittacinepox virus, (Poxyiridae), Puchong virus, (Rhabdoviridae), Pueblo Viejo virus, (Bunyaviridae), Puffin Island virus, (Bunyaviridae), Punta Salinas virus, (Bunyaviridae), Punta Toro virus, (Bunyaviridae), Purus virus, (Reoviridae), Puumala virus, (Bunyaviridae), Qalyub virus, (Bunyaviridae), Quailpox virus, (Poxyiridae), Quokkapox virus, (Poxyiridae), Rabbit coronavirus, (Coronaviridae), Rabbit fibroma virus, (Poxyiridae), Rabbit hemorrhagic disease virus, (Caliciviridae), Rabbit kidney vacuolating virus, (Papovaviridae), Rabbit oral papillomavirus, (Papovaviridae), Rabbitpox virus, (Poxyiridae), Rabies virus, (Rhabdoviridae), Raccoon parvovirus, (Parvoviridae), Raccoonpox virus, (Poxyiridae), Radi virus, (Rhabdoviridae), Rangifer tarandus herpesvirus, (Herpesviridae), Ranid herpesvirus, (Herpesviridae), *Raphanus* virus, (Rhabdoviridae), Rat coronavirus, (Coronaviridae), Rat cytomegalovirus, (Herpesviridae), Rat virus, R, (Parvoviridae), Raza virus, (Bunyaviridae), Razdan virus, (Bunyaviridae), Red deer herpesvirus, (Herpesviridae), Red kangaroopox virus, (Poxyiridae), Reed Ranch virus, (Rhabdoviridae), herpesvirus, (Herpesviridae), Reindeer papillomavirus, (Papovaviridae), Reptile calicivirus, (Caliciviridae), Resistencia virus, (Bunyaviridae), Restan virus, (Bunyaviridae), Reticuloendotheliosis virus, (Retroviridae), Rhesus HHV-like virus, (Herpesviridae), Rhesus leukocyte associated herpesvirus strain, (Herpesviridae), Rhesus monkey cytomegalovirus, (Herpesviridae), Rhesus monkey papillomavirus, (Papovaviridae), Rheumatoid arthritis virus, (Parvoviridae), Rift Valley fever virus, (Bunyaviridae), Rinderpest virus, (Paramyxoviridae), Rio Bravo virus, (Flaviviridae), Rio Grande virus, (Bunyaviridae), RML virus, (Bunyaviridae), Rochambeau virus, (Rhabdoviridae), Rocio virus, (Flaviviridae), Ross River virus, (Togaviridae), Rost Islands virus, (Reoviridae), Rous sarcoma virus, (Retroviridae), Royal farm virus, (Flaviuiridae), RT parvovirus, (Parvoviridae), Rubella virus, (Togaviridae), Russian spring summer encephalitis virus, (Flaviviridae), S-virus, (Reoviridae), SA virus, (Herpesviridae), Sabio virus, (Arenaviridae), Sabo virus, (Bunyaviridae), Saboya virus, (Flaviviridae), Sacbrood virus, (Picornaviridae), Sagiyama virus, (Togaviridae), Saimiriine herpesvirus, (Herpesviridae), SaintAbb's Head virus, (Reoviridae), Saint-Floris virus, (Bunyaviridae), Sakhalin virus, (Bunyaviridae), Sal Vieja virus, (Flaviviridae), Salanga virus, (Bunyaviridae), Salangapox virus, (Poxyiridae), Salehabad virus, (Bunyaviridae), Salmonid herpesvirus, (Herpesviridae), Salmonis virus, (Rhabdoviridae), *Sambucus* vein clearing virus, (Rhabdoviridae), SanAngelo virus, (Bunyaviridae), San Juan virus, (Bunyaviridae), San Miguel sealion virus, (Caliciviridae), San Perlita virus, (Flaviviridae), Sand rat nuclear inclusion agents, (Herpesviridae), Sandfly fever Naples virus, (Bunyaviridae), Sandfly fever Sicilian virus, (Bunyaviridae), Sandjimba virus, (Rhabdoviridae), Sango virus, (Bunyaviridae), Santa *Rosa* virus, (Bunyaviridae), Santarem virus, (Bunyaviridae), Sapphire II virus, (Bunyaviridae), Saraca virus, (Reoviridae), Sarracenia purpurea virus, (Rhabdoviridae), Sathuperi virus, (Bunyaviridae), Saumarez Reef virus, (Flaviviridae), Sawgrass virus, (Rhabdoviridae), Schistocerca gregaria entomopoxvirus, (Poxyiridae), Sciurid herpesvirus, (Herpesviridae), Sciurid herpesvirus, (Herpesviridae), Sealpox virus, (Poxyiridae), Seletar virus, (Reoviridae) Semliki Forest virus, (Togaviridae), Sena Madureira virus, (Rhabdoviridae), Sendai virus, (Paramyxoviridae), Seoul Virus, (Bunyaviridae), Sepik virus, (Flaviviridae), Serra do Navio virus, (Bunyaviridae), Shamonda virus, (Bunyaviridae), Shark River virus, (Bunyaviridae), Sheep associated malignant catarrhal fever of, (Herpesviridae), Sheep papillomavirus, (Papovaviridae), Sheep pulmonary adenomatosis associated herpesvirus, (Herpesviridae), Sheeppox virus, (Poxyiridae), Shiant Islands virus, (Reoviridae), Shokwe virus, (Bunyaviridae), Shope fibroma virus, (Poxyiridae), Shuni virus, (Bunyaviridae), Sibine fusca densovirus, (Parvoviridae), Sigma virus, (Rhabdoviridae), Sikte water-borne virus, (Tombusviridae), Silverwater virus, (Bunyaviridae), virus, (Bunyaviridae), Simian adenoviruses, (Adenoviridae), Simian agent virus, (Papovaviridae), Simian enterovirus, (Picornaviridae), Simian foamy virus, (Retroviridae), Simian hemorrhagic fever virus, (Arterivirus), Simian hepatitis A virus, (Picornaviridae), Simian immunodeficiency virus, (Retroviridae), Simian parainfluenza virus, (Paramyxoviridae), Simian rotavirus SA, (Reoviridae), Simian sarcoma virus, (Retroviridae), Simian T-lymphotropic virus, (Retroviridae), Simian type D virus, (Retroviridae), Simian vancella herpesvirus, (Herpesviridae), Simian virus, (Papovaviridae), Simulium vittatum densovirus, (Parvoviridae), Sindbis virus, (Togaviridae), Sixgun city virus, (Reoviridae), Skunkpox virus, (Poxyiridae), Smelt reovirus, (Reoviridae), Snakehead rhabdovirus, (Rhabdoviridae), Snowshoe hare virus, (Bunyaviridae), Snyder-Theilen feline sarcoma virus, (Retroviridae), Sofyn virus, (Flaviviridae), Sokoluk virus, (Flaviviridae), Soldado virus, (Bunyaviridae), Somerville virus, (Reoviridae), Sparrowpox virus, (Poxyiridae), Spectacled caimanpox virus, (Poxyiridae), SPH virus, (Arenaviridae), Sphenicid herpesvirus, (Herpesviridae), Spider monkey herpesvirus, (Herpesviridae), Spondweni virus, (Flaviviridae), Spring viremia of carp virus, (Rhabdoviridae), Squirrel fibroma virus, (Poxyiridae), Squirrel monkey herpesvirus, (Herpesviridae), Squirrel monkey retrovirus, (Retroviridae), SR-virus, (Bunyaviridae), Sripur virus, (Rhabdoviridae), StAbbs Head virus, (Bunyaviridae), St. Louis encephalitis virus, (Flaviviridae), Starlingpox virus, (Poxyiridae), Stratford virus, (Flaviviridae), Strigid herpesvirus, (Herpesviridae), Striped bass reovirus, (Reoviridae), Striped Jack nervous necrosis virus, (Nodaviridae), Stump-tailed macaque virus, (Papovaviridae), Suid herpesvirus, (Herpesviridae), Sunday Canyon virus, (Bunyaviridae), Sweetwater Branch virus, (Rhabdoviridae), Swine cytomegalovirus, (Herpesviridae), Swine infertility and respiratory syndrome virus, (Arterivirus), Swinepox virus, (Poxyiridae), Tacaiuma virus, (Bunyaviridae), Tacaribe virus, (Arenaviridae), Taggert virus, (Bunyaviridae), Tahyna virus, (Bunyaviridae), Tai virus, (Bunyaviridae), Taiassui virus, (Bunyaviridae), Tamana bat virus, (Flaviviridae), Tamdy virus, (Bunyaviridae), Tamiami virus, (Arenaviridae), Tanapox virus, (Poxyiridae), Tanga virus, (Bunyaviridae), Tanjong Rabok virus, (Bunyaviridae), Taro bacilliform virus, (Badnavirus), Tataguine virus, (Bunyaviridae), Taterapox virus, (Poxyiridae), Tehran virus, (Bunyaviridae), Telok Forest virus, (Bunyaviridae), Tembe virus, (Reoviridae), Tembusu virus, (Flaviviridae), Tench reovirus, (Reoviridae), Tensaw virus, (Bunyaviridae), Tephrosia symptomless virus, (Tombusviridae), Termeil virus, (Bunyaviridae), Tete virus, (Bunyaviridae), Thailand virus, (Bunyaviridae), Theiler's murine encephalomyelitis virus, (Picornaviridae), Thermoproteus virus, Lipothrixviridae, Thiafora virus, (Bunyaviridae), Thimiri virus, (Bunyaviridae), Thogoto virus, (Orthomyxoviridae), Thormodseyjarklettur virus, (Reoviridae), Thottapalayam virus, (Bunyaviridae), Tibrogargan virus, (Rhabdoviridae), Tickborne encephalitis virus, (Flaviviridae), Tillamook virus, (Bunyaviridae), Tilligerry virus, (Reoviridae), Timbo virus, (Rhabdoviridae), Tilmboteua virus, (Bunyaviridae), Tilmaroo virus, (Bunyaviridae), Tindholmur virus, (Reoviridae), Tlacotalpan virus, (Bunyaviridae), Toscana virus, (Bunyaviridae), Tradescantia/Zebrina virus, Potyviridae, Trager duck spleen necrosis virus, (Retroviridae), Tree shrew adenovirus, (Adenoviridae), Tree shrew herpesvims, (Herpesviridae), Triatoma virus, (Picornaviridae), Tribec virus, (Reoviridae), Trivittatus virus, (Bunyaviridae), Trombetas virus, (Bunyaviridae), Trubanarnan virus, (Bunyaviridae), Tsuruse virus, (Bunyaviridae), Tucunduba virus, (Bunyaviridae), Tumor virus X, (Parvoviridae), Tupaia virus, (Rhabdoviridae), Tupaiid herpesvirus, (Herpesviridae), Turbot herpesvirus, (Herpesviridae), Turbot reovirus, (Reoviridae), Turkey adenoviruses, (Adenoviridae), Turkey coronavirus, (Coronaviridae), Turkey herpesvirus, (Herpesviridae), Turkey rhinotracheitis virus, (Paramyxoviridae), Turkeypox virus, (Poxyiridae), Turlock virus, (Bunyaviridae), Turuna virus, (Bunyaviridae), Tyuleniy virus, (Flaviviridae) Uasin Gishu disease virus, (Poxyiridae), Uganda S virus, (Flaviviridae), Ulcerative disease rhabdovirus, (Rhabdoviridae), Umatilla virus, (Reoviridae), Umbre virus, (Bunyaviridae), Una virus, (Togaviridae), Upolu virus, (Bunyaviridae), UR sarcoma virus, (Retroviridae), Urucuri virus, (Bunyaviridae), Usutu virus, (Flaviviridae), Uting a virus, (Bunyaviridae), Utive virus, (Bunyaviridae), Uukuniemi virus, (Bunyaviridae) Vaccinia subspecies, (Poxyiridae), Vaccinia virus, (Poxyiridae), Vaeroy virus, (Reoviridae), Varicella-zoster virus, (Herpesviridae), Variola virus, (Poxyiridae), Vellore virus, (Reoviridae), Venezuelan equine encephalitis virus, (Togaviridae), Vesicular exanthema of swine virus, (Caliciviridae), Vesicular stomatitis Alagoas virus, Rkabdoviridae, Vesicular stomatitis Indiana virus, (Rhabdoviridae), Vesicular stomatitis New Jersey virus, (Rhabdoviridae), Vilyuisk virus, (Picornaviridae), Vinces virus, (Bunyaviridae), Viper retrovirus, (Retroviridae), Viral hemorrhagic septicemia virus, (Rhabdoviridae), Virgin River virus, (Bunyaviridae), Virus III, (Herpesviridae), Visna/maedi virus, (Retroviridae), Volepoxvirus, (Poxyiridae), Wad Medani virus, (Reoviridae), Wallal virus, (Reoviridae), Walleye epidermal hyperplasia, (Herpesviridae), Wanowrie virus, (Bunyaviridae), Warrego virus, (Reoviridae), Weddel water-borne virus, Tombusviridae, Weldona virus, (Bunyaviridae), Wesselsbron virus, (Flaviviridae), West Nile virus, (Flaviviridae), Western equine encephalitis virus, (Togaviridae), Wexford virus, (Reoviridae), Whataroa virus, (Togaviridae), Wildbeest herpesvirus, (Herpesviridae), Witwatersrand virus, (Bunyaviridae), Wongal virus, (Bunyaviridae), Wongorr virus, (Reoviridae), Woodchuck hepatitis B virus, (Hepadnaviridae), Woodchuck herpesvirus marmota, (Herpesviridae), Woolly monkey sarcoma virus, (Retroviridae), Wound tumor virus, (Reoviridae), WVU virus, (Reoviridae), WW virus, (Reoviridae), Wyeomyia virus, (Bunyaviridae), Xiburema virus, (Rhabdoviridae), Xingu virus, (Bunyaviridae), Y sarcoma virus, (Retroviridae), Yaba monkey tumor virus, (Poxyiridae), Yaba-virus, (Bunyaviridae), Yaba-virus, (Bunyaviridae), Yacaaba virus, (Bunyaviridae), Yaounde virus, (Flaviviridae), Yaquina Head virus, (Reoviridae), Yata virus, (Rhabdoviridae), Yellow fever virus, (Flaviviridae), Yogue virus, (Bunyaviridae), Yokapox virus, (Poxyiridae), Yokase virus, (Flaviviridae), Yucca baciliform virus, Badnavirus, Yug Bogdanovac virus, (Rhabdoviridae), Zaliv Terpeniya virus, (Bunyaviridae), *Zea mays* virus, (Rhabdoviridae), Zegla virus, (Bunyaviridae), Zika virus, (Flaviviridae), Zirqa virus, (Bunyaviridae).

DETAILED DESCRIPTION OF THE INVENTION

The present invention relates to a composition in a pharmaceutically effective concentration comprising a compound of Formula A being

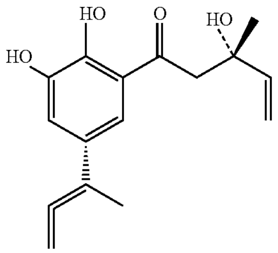

and/or a compound of Formula B being

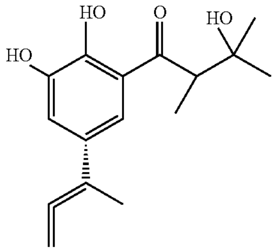

and/or a compound of Formula C being

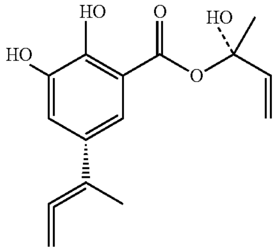

for use as a medicament.

Formula A ($C_{16}H_{18}O_4$) of the present invention corresponds to the compound: 2,3(dihydroxy), 5[3(1,2)butadiene], 1(3hydroxy,3-methyl,4-pentene)benzene.

Formula B ($C_{16}H_{20}O_4$) of the present invention corresponds to the compound: 2,3(dihydroxy), 5[3(1,2)butadiene], 2[2-methylbutane]benzenal.

Formula C($C_{15}H_{16}O_5$) of the present invention corresponds to the compound: 2,3(dihydroxy), 5[3(1,2)butadiene], 2hydroxy,3butene benzoate.

The present invention relates also to a composition in a pharmaceutically effective concentration comprising a compound of the Formula A being

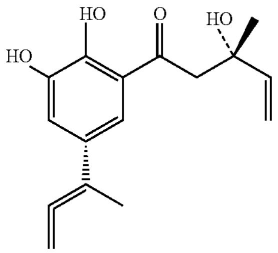

and/or a compound of the Formula B being

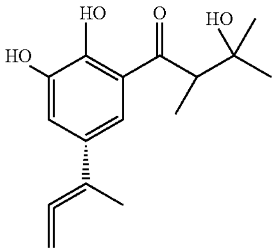

and/or a compound of the Formula C being

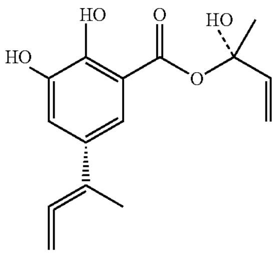

for in vivo use in treatment and prevention of diseases caused by DNA enveloped viruses, DNA non-enveloped viruses, RNA enveloped viruses and RNA non-enveloped viruses, said diseases are selected from the group consisting in: (broncho)-pneumonia, 3 day fever exanthema, acute and chronic hepatitis, acute fever, acute gastroenteritis caused by strains such as Desert Shield Lordsdale Mexico Norwalk Hawaii Snow Mountain Southampton virus, acute gastroenteritis caused by strains such as Houston/86 Houston/90 London 29845 Manchester Parkville Sapporo virus, acute hepatitis, acute respiratory distress syndrome, AIDS, Argentine hemorrhagic fever, arthralgia, avian flu, Bolivian hemorrhagic fever, Brazilian hemorrhagic fever, chickenpox, chronic hepatitis, coma, common cold infection, common cold symptoms, congenital infection, conjunctivitis, contagious eethyma, contagious pustular dermatitis, cornea, cryptic enteric infection, cytomegaloviral mononucleosis, dengue hemorrhagic fever (DHF), dengue shock syndrome (DSS), diarrhea, eczema, eczema herpaticum, encephalitis, encephalopathy, enteritis, epidemic nephropathy, epidemic polyarthritis and exanthema, epidermodysplasia veruciformis, Epstein-Barr virus infection, exanthema, exanthema in children, Fatal familial insomnia, febrile encephalitis, febrile illness, fever, formerly Human echovirus 22 23, gastroenteritis, gastrointestinal infections intracytoplasmic inclusion bodies, genital tract infections, haemolytic crisis in people with sickle cell disease, headaches, hemorrhagic fever, hemorrhagic fever w renal syndrome, herpetic encephalitis, Hodgkin's disease, Human coxsackievirus, Human coxsackievirus B1-6, Human echovirus 1-7 9 11-21 24-27 29-33, Human enterovirus 69, Human enterovirus 71 (hand foot and mouth disease), Human hepatitis virus A (HHAV), Human poliovirus, Human rhinovirus 1 2 7 9 11 15 16 21 29 36 39 49 50 58 62 65 85 89 hyperacute respiratory disease, Human rhinovirus 3 14 72, hyperacute respiratory disease, immune deficiency syndrome, infantile diarrhea, Infection with any dengue serotype (1-4), infectious mononucleosis, joint pain, Kaposi's sarcoma, keratoconjunctivitis, lesions of coutanous sites, leucopoenia, liver cirrhosis, lower respiratory tract infection, lymphadenopathy, maculopapular rash, measles, meningitis, mononucleosis (kissing disease), mumps, muscle pains, myocarditis, nephropathy, nephropathy in transplant patients, numbness, opportunistic infection, oral infections, orchitis, pancreatitis, pandemics, papilloma, paralysis, persistent infection of the kidney, persistent infections, persistent lymphopathy, pharyngeal conjunctivitis, pneumonia, primary hepatocellular carcinoma, pulmonary syndrome, rabies, rash, recurrent epidemics of respiratory disease, respiratory disease, respiratory illness, Roseola infantum, sarcoma, sever chills arthralgia, severe acute respiratory syndrome, severe encephalitis, shingles, sixth disease, skin and mucous membrane lesions, slim disease, sore throat, subacute sclerosing panencephalitis, superinfection with Deltavirus, ulceration, upper respiratory tract illness, Venezuelan hemorrhagic fever, vesicular pharyngitis, vesicular stomatitis with exanthema, viral polyarthritis and rush, viral warts, watery diarrhea, weakness, zoonotic, zoster, metaplasia, dysplasia, anaplasia, desmoplasia, carcinoma in situ, flu (influenza), invasive carcinoma.

The composition of the present invention can be used as a prophylactic or as a viral inhibitor within or outside the body.

The composition of the present invention can be administered, orally, topically, by inhalation, by suppository, intravenously, subcutaneously, intramuscularly or via patch. It is also possible to spray a condom with the composition of the present invention if said composition is intended to treat sexual transmitted diseases. The composition of the present invention can be manufactured in form of a solid (powder, tablets), or semi solid (creams, foams) or in form of a liquid or in form of a gas (aerosol).

The composition of the present invention can be used as a disinfectant or as a viral inhibitor outside the body.

The composition of the present invention is used for blocking the above mentioned viruses entering the host cell(s).

The composition of the present invention consists in:

the compound of formula A alone, or the compound of formula B alone, or the compound of formula C alone, or the compound of formula A in combination with the compound of formula B (i.e. A+B), or the compound of formula A in combination with the compound of formula C (i.e. A+C), or the compound of formula B in combination with the compound of formula C (i.e. B+C), or the compound of formula A in combination with the compound of formula B and also in combination with the compound of formula C (i.e. A+B+C).

The composition preferably comprises 100% by weight of the compound of formula A, or 100% by weight of the compound of formula B, or 100% by weight of the compound of formula C.

Thus the following compositions can be prepared (in terms of formulae):

Composition 1: A alone (100% by weight)

Composition 2: B alone (100% by weight)

Composition 3: C alone (100% by weight)

The compositions 1, 2 and 3 of the present invention can also be diluted in a base oil (50% by weight of a base oil or 60% by weight or 70% by weight or 80% by weight or 90% by weight). The base oil can be olive oil or *macadamia* oil, preferably at 50% by weight of the base oil.

The compound of formula A can alternatively be added in the composition of the present invention with either the compound of formula B or the compound of formula C or both compounds of formula B and C. The compound of formula B can also only be added with the compound of formula C in the composition of the present invention. Thus the following combinations can be prepared (in terms of formulae):

Composition 4: A+B (90% by weight of A/10% by weight of B)

Composition 5: A+C (50% by weight of A/50% by weight of C)

Composition 6: A+B+C (45% by weight of A/10% by weight of B/45% by weight of C)

Composition 7: B+C (10% by weight of B/90% by weight of C)

The compositions 4, 5, 6 and 7 of the present invention can also be diluted in a base oil as mentioned above.

Each compound of the present invention can be administered at a dose higher than or equal to 0.1 mg per administering, preferably at a dose comprised between 0.1 mg and 5000 mg per administering, most preferably between 10 mg and 500 mg. The dose can be administered 1 or 2 or 3 times or more per day.

In the unprobable case that one or more of the above mentioned compounds would have been known from a prior art document, we reserve the right to disclaim such compound from the present invention.

The man skilled in the art would know how to manufacture the compounds of formulae A, B or C.

Preparation of the Compound of Formula A

The compound of Formula A can be prepared in combining 3 different compounds (Xa, Ya and Za defined as follows), namely:

Xa: $C_6H_4(OH)_2$: catechol

Ya: $H_2C{=}C{=}C(Cl){-}CH_3$: 3-chloro-(1,2)butadiene

Za: $H_2C{=}CH{-}C(CH_3)(OH){-}CH_2{-}COCl$: 1-chloro-3-OH-3-methyl-4-ene-pentanal Preparation of Ya:

$$H_2C{=}C{=}CH{-}CH_3 \xrightarrow[HCl/Cl^-]{\text{halogenation}} H_2C{=}C{=}C(Cl){-}CH_3$$

Preparation of Za:

$$H_2C{=}CH{-}C(CH_3){=}CH{-}COOH \xrightarrow[HCl]{Cl^-} \xrightarrow[OH^-/H^+]{H_2O} H_2C{=}CH{-}C(CH_3)(OH){-}CH_2{-}COCl$$

Formula $A=(Xa+Za)+Ya$

A man skilled in the art is able to manufacture the compound of formula A with the above mentioned information.

Preparation of the Compound of Formula B

The compound of Formula B can be prepared in combining 3 different compounds (Xb, Yb and Zb defined as follows), namely:

Xb: $C_6H_4(OH)_2COCl$

Yb: $H_2C{=}C{=}C(Cl){-}CH_3$: 3-chloro-(1,2)butadiene

Zb: $H_3C{-}C(CH_3)(OH){-}CH_2{-}CH_3$:2 hydroxy,2-methylbutane

Preparation of Xb:

$$C_6H_4(OH)_2COOH \xrightarrow[HCl/Cl^-]{\text{halogenation}} C_6H_4(OH)_2COCl$$

Preparation of Yb:

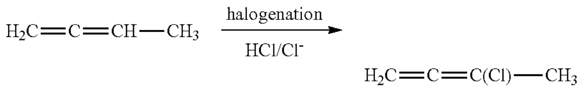

Preparation of Zb:

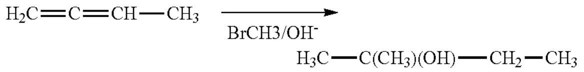

Formula $B=(Xb+Yb)+Zb$

A man skilled in the art is able to prepare the compound of formula B with the above mentioned information.

Preparation of the Compound of Formula C

The compound of Formula C can be prepared in combining 3 different compounds (Xc, Yc and Zc defined as follows), namely:

Formula $C=(Xc+Zc)+Yc$

First Step:

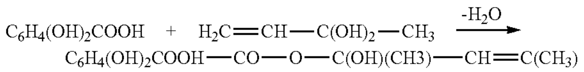

Second Step:

$C_6H_4(OH)_2COOH$—CO—O—C(OH)(CH3)-CH=C($CH_3$)+$H_2C$=C=C(Cl)—$CH_3$→2,3(dihydroxy), 5[3(1,2)butadiene], 2hydroxy,3butene benzoate A man skilled in the art is able to prepare the compound of formula C with the above mentioned information.

Advantage of the Present Invention

An advantage of the antiviral composition(s) according to the present invention consists in that no simultaneous resistance can be developed by the viruses. Moreover, the non-specific activity of the composition(s) according to the invention is different to that of conventional drugs, enabling them to effectively treat and prevent diseases and not to be affected by the possible emergence of virus mutation.

Another advantage of the compositions according to the invention is that the compounds are lipophilic, being therefore able to easily cross between body and cellular compartments and accumulate in lipid-rich tissues.

Being volatile, the compounds of the composition(s) according to the invention can be excreted via the lungs: an added advantage when treating and preventing respiratory infections or inflammations. The compounds of the composition can be diffused into the atmosphere and fall onto exposed surface, deactivating viruses before they reach a potential host.

In order to prove the efficacy of the composition of the present invention, in vivo studies have been conducted. Following are examples of at least one virus belonging to each of the 4 major viral families.

In Vivo Tests:

Individual case studies were performed by medical practitioners that confirmed the potent activity of the composition(s) of the present invention against all existing 4 families of viruses, namely:

DNA enveloped viruses (e.g. Herpes virus, Molluscum contagiosum, Varicella-zoster).

DNA non-enveloped viruses (e.g. Papillomavirus, Parvovirus, Adenovirus).

RNA enveloped viruses (e.g. Hepatitis C, Porcine reproductive and respiratory syndrome virus (PPRS virus), Coronavirus).

RNA non-enveloped viruses (e.g. Rotavirus, Rhinovirus, Coxsackievirus).

Mode of Action

The composition(s) of the present invention deactivate(s) viruses when they are in the free state, i.e. when they are not associated with cells, by interfering with the surface tension of the lipid coating of the viruses capsules thereby preventing the entry of the viruses in the animal or human cells and therefore the multiplication of the viruses in the cells. This had been determined by in vitro technology. This is in direct contrast to existing antiviral products, which only exert an effect once the viruses are associated with host cells. The composition(s) of the present invention can act as an anti-infectious agent, inactivating viral particles before they contact the host. There is only one common mode of action of the composition(s) of the present invention involved in all diseases; therefore there should be no need to provide tests for all diseases or all viruses specifically mentioned in the present application.

Compounds A, B and C, as well as compositions A+B, A+C, B+C and A+B+C are unitary in the fact that they all have the same mode of action.

In Vivo Results:

The following examples have been taken from cases study results to highlight the activity of the antiviral composition for which the specific composition have been used in order to conduct all the mentioned tests. In the present invention the novel composition is always instilled on or in animals after the viruses infected the animal in order to treat animal or human diseases. The man skilled in the art knows how to perform the tests.

Tests Results Conclusions:

Independently of the fact that the treated viruses belonged to the RNA, DNA, enveloped or non-enveloped groups, the composition(s) of the present invention interferes with the existing or acquired lipid envelope covering the virus and not with the virus per se; all studies indicate that the composition is capable of de-activating every type of virus in a free state.

Administration of the Composition:

The best mode administering the composition is one drop or 0.05 ml per 10 kg body weight (not including excess body fat), three times daily orally. The man skilled in the art can adapt the recommended dose per kg to the average weight of a human (50 kg). Preferably encapsulated but can be taken orally mixed with fruit juice or yoghurt, topically mixing with *macadamia*-type oil for fast skin absorption and petroleum jelly for slow topical absorption. For administering to animals composition can be mixed with the feed. Aerosol or topical application according to standard aerosol dispersions methods. Rectal or vaginal insertion of suppository with indicated dose according to standard suppository administration methods.

For topical applications like the treatment of warts, the best mode of administering is the use of a micro dropper or 0.01 ml containing 50 wt. % of base oil and 50 wt. % of the composition of the present invention. An alternative method of administering is the use of a wax stick containing 30 wt. % of the composition of the present invention. In this mode of application the effective dosage can be as low as 0.1 mg of the composition per treated wart.

Process of Manufacture and Galenics:

Preferably the compounds have to be pre-blended (in case at least two compounds are added into the composition or if a base oil is added), in equal or different parts, using a sterile blending device. The preferred temperature of manufacturing and storage of the composition is between 20 and 25 degrees Celcius.

After the pre-blending process the mixture can be added to a pharmaceutically acceptable carrier. Depending on the type of application, the ratio between the composition of the present invention and the pharmaceutically acceptable carrier can range from 5 wt. % to 90 wt. %, where 50 wt. % is the most common ratio used for practical medical applications.

The mixture can then be further processed and integrated in capsules, gels, gelules, sprays, aerosols, suppositories, wax sticks, patches or other drug delivery vehicles.

The method for manufacturing the compositions of the present invention comprises the following steps:

pre-blending the compound(s) of the present invention at a temperature comprised preferably between 20 and 25° C., Preparation of a mixture, addition of the mixture to a diluent (a pharmaceutically acceptable carrier such as a base oil).

The presence of a pharmaceutically acceptable carrier is optional and depends on the type of drug delivery vehicle.

The person skilled in the art knows how to manufacture the compositions of the present invention.

EXAMPLES

Preparation of the Composition and Examples of Efficacy Compound of Formula A The letters A, B, C in the examples refer to the compounds of formula A, formula B, formula C respectively of the present invention.

Preparation of the Medication

The compound of formula A is a clear liquid, which may be mixed with a base oil such as Olive or *Macadamia* oil, preferably at a rate of 50 wt. %.

In vivo Antiviral Activity of the Compound of Formula A

Example 1

DNA-Enveloped Viruses: Canine Herpes

Canine Herpes virus is a leading case of puppy deaths. It lives in the respiratory and reproductive tracts of adult dogs, which show no symptoms. It is transferred to puppies during birth or via airborne nasal secretions once born. It is very contagious and spreads rapidly through litters, causing liver damage, hemorrhages, blindness and staggering. Death occurs within 24-48 hours. There is no conventional cure and treatment aimed at supportive care. Vaccination does not exist.

One confirmed Canine Herpes infected puppy was treated immediately with 300 mg of the compound of formula A, three times a day for 4 days. The puppy, which under normal circumstances would have died, showed signs of recovery on/after the second day of treatment.

The puppy was confirmed Herpes free after the $4^{th}$ day of treatment.

The puppy recovered completely after 10 days.

Example 2

DNA-Non-Enveloped Viruses: Parvo Virus

Parvovirus is a highly contagious disease and major killer of puppies. It is characterized by bloody diarrhea and progresses rapidly, with death occurring often within 2 to 6 days. It is transmitted via infected faeces.

A puppy from a nest of confirmed Parvo infected puppies was treated immediately with 300 mg of the compound of formula A, three times a day for 4 days. The puppy, which under normal circumstances would have died, showed signs of recovery on/after the first day of treatment.

The puppy was confirmed Parvo free after the $4^{th}$ day of treatment.

The puppy recovered completely after 6 days.

Example 3

RNA-Enveloped Viruses: PRRS

PRRS—Porcine Reproductive and Respiratory Syndrome—is a major cause of disease in pigs; it is present in virtually all pig herds with 100% of adults being sero-positive. The disease is characterized by abortion and stillbirths in adults and respiratory disease, diarrhea and poor growth characteristics in piglets.

2 PRRS confirmed piglets were treated immediately with 500 mg of the compound of formula A, three times a day for 4 days. The piglets, which were very week at the start of the treatment and would recover at best after 7-10 days, showed signs of recovery on/after one day of treatment.

The piglets were confirmed PRRS free after the $2^{th}$ day of treatment.

The piglets recovered completely after 4 days.

Example 4

RNA-Non-Enveloped Viruses: Rota Virus

Three piglets with confirmed Rotavirus infections were treated immediately with 500 mg of the compound of formula A, three times a day for 2 days. All three piglets, which would normally experience 3 to 4 days of severe symptoms including diarrhea stopped having diarrhea on/after one day. The de-activation of the Rota virus infected was confirmed on/after the second day. The piglets recovered completely within 2 days.

Preparation of the Medical Composition and Examples of Efficacy

Compound of Formula B

Preparation of the Medication of the Compound of Formula B

The compound of formula B is a clear liquid, which preferably is mixed with a base oil such as Olive or *Macadamia* oil, preferably at a rate of 10 wt. % or 20 wt. % of the compound of formula B and of 90 wt. % or 80 wt. % respectively of a base oil.

In vivo Antiviral Activity of the Compound of Formula B

Example 1

DNA-Enveloped Viruses: Herpes Labialis

Herpes labialis is a common disease caused by infection of the mouth area with herpes simplex virus type 1. Most people are infected with this virus by age of 20 years. An outbreak usually involves skin lesions or rash around the lips, mouth, and gums. Untreated, the symptoms will generally go away in 1 to 2 weeks.

One confirmed Herpes Labialis patient who traditionally had Herpes severe lesions that lasted two weeks was treated topically immediately on the onset of the lesions with 10 mg of the compound of formula B, three times a day for 1 day. The infection did not get worse and the lesions started to disappear on/after the second day.

The patient had no more signs of infection after the $4^{th}$ day.

Example 2

DNA-Non-Enveloped Viruses: Papilloma Virus

A wart is generally a small, rough growth, typically on a human's hands or feet but often other locations, that can resemble a cauliflower or a solid blister. They are caused by a viral infection, specifically by human papilloma virus 2 and 7. There are more than 10 varieties of warts, the most common considered to be mostly harmless.

Skin warts usually remain infected for years. Topically treatment exists but requires usually 3 to 5 treatments a day for 2 to 3 months (over 200 treatments minimum).

Skin warts of patient were treated with 10 mg of the compound of formula B, three times a day for 3 days.

The warts started to soften on/after a week and becoming white.

The skin tissue disappeared completely after 3 weeks.

Example 3

RNA-Enveloped Viruses: PRRS

PRRS—Porcine Reproductive and Respiratory Syndrome—is a major cause of disease in pigs; it is present in virtually all pig herds with 100% of adults being sero-positive. The disease is characterized by abortion and stillbirths in adults and respiratory disease, diarrhea and poor growth characteristics in piglets.

Two PRRS confirmed piglets were treated immediately with 50 mg of the compound of formula B, six times a day for 3 days. The piglets, which were very week at the start of the treatment and would recover at best after 7-10 days, showed signs of recovery after the second day of treatment.

The piglets were confirmed PRRS free on/after the $3^{rd}$ day of treatment.

The piglets recovered completely after 4 days.

Example 4

RNA-Non-Enveloped Viruses: Rota Virus

Three piglets with confirmed Rotavirus infections were treated immediately with 50 mg of the compound of formula B, six times a day for 2 days. All 3 piglets, which would normally experience 4 to 5 days of severe symptoms including diarrhea stopped having diarrhea on/after the second day.

The de-activation of the Rota virus infected was confirmed on/after the second day.

The piglets recovered completely within 3 days.

Compound of Formula C

Preparation of the Medication of the Compound of Formula C

The compound of formula C is a clear liquid, which preferably is mixed with a base oil such as Olive or *Macadamia* oil preferably at a rate of 50 wt. %.

In vivo Antiviral Activity of the Compound of Formula C

Example 1

DNA-Enveloped Viruses: Canine Herpes

Canine Herpes virus is a leading case of puppy deaths. It lives in the respiratory and reproductive tracts of adult dogs, which show no symptoms. It is transferred to puppies during birth or via airborne nasal secretions once born. It is very contagious and spreads rapidly through litters, causing liver damage, hemorrhages, blindness and staggering. Death occurs within 24-48 hours. There is no conventional cure and treatment is aimed at supportive care. Vaccination does not exist.

One confirmed Canine Herpes infected puppy was treated immediately with 300 mg of the compound of formula C, three times a day for 4 days. The puppy, which under normal circumstances would have died, showed signs of recovery on/after the 2nd day of treatment.

The puppy was confirmed Herpes free after the $4^{th}$ day of treatment.

The puppy recovered completely after 7 days.

Example 2

DNA-Non-Enveloped Viruses: Parvo Virus

Parvovirus is a highly contagious disease and major killer of puppies. It is characterized by bloody diarrhea and progresses rapidly, with death occurring often within two days. It is transmitted via infected faeces.

One puppy from a nest of confirmed Parvo infected puppies was treated immediately with 300 mg of the compound of formula C, three times a day for 4 days. The puppy, which under normal circumstances would have died, showed signs of recovery on/after the first day of treatment.

The puppy was confirmed Parvo free on/after the $4^{th}$ day of treatment.

The puppy recovered completely after 6 days.

Example 3

RNA-Enveloped Viruses: PRRS

PRRS—Porcine Reproductive and Respiratory Syndrome—is a major cause of disease in pigs; it is present in virtually all pig herds with 100% of adults being sero-positive. The disease is characterized by abortion and stillbirths in adults and respiratory disease, diarrhea and poor growth characteristics in piglets.

2 PRRS confirmed piglets were treated immediately with 500 mg of the compound of formula C, three times a day for 4 days. The piglets, which were very week at the start of the treatment and would recover at best after 7-10 days, showed signs of recovery on/after one day of treatment.

The piglets were confirmed PRRS free on/after the $2^{nd}$ day of treatment.

The piglets recovered completely after 4 days.

Example 4

RNA-Non-Enveloped Viruses: Rota Virus 2 piglets with confirmed Rotavirus infections were treated immediately with 500 mg of the compound of formula C, three times a day for 2 days. Both piglets, which would normally experience 3 to 4 days of severe symptoms including diarrhea stopped having diarrhea after one day.

The de-activation of the Rota virus infected was confirmed on/after the first day.

The piglets recovered completely within 2 days.

Preparation of the Medical Composition and Examples of Efficacy

Composition Containing the Combination of Formula A and Formula B (A+B)

Preparation of the Medication of the Composition Containing the Combination A+B

The composition containing the combination of formula A+B is a clear liquid, which preferably is mixed with a base oil such as Olive or *Macadamia* oil, preferably at a rate of 10 wt. % of A and 10 wt. % of B and 80 wt % of base oil.

In vivo Antiviral Activity of the Composition Containing the Combination a+B

Example 1

DNA-Enveloped Viruses: Herpes Labialis

Herpes labialis is a common disease caused by infection of the mouth area with herpes simplex virus type 1. Most people are infected with this virus by the age of 20 years. An outbreak usually involves skin lesions or rash around the lips, mouth and gums. Untreated, the symptoms will generally go away in 1 to 2 weeks.

One confirmed Herpes Labialis patient who traditionally had Herpes severe lesions that lasted two weeks was treated topically immediately on the onset of the lesions with 10 mg of the compound of formula A+B, three times a day for 1 day. The infection did not get worse and the lesions started to disappear on/after the 2nd day.

The patient had no more signs of infection after the 4th day.

Example 2

DNA-Non-Enveloped Viruses: Papilloma Virus

A wart is generally a small, rough growth, typically on a human's hands or feet but often other locations, that can resemble a cauliflower or a solid blister. They are caused by a viral infection, specifically by human papilloma virus 2 and 7. There are more than 10 varieties of warts, the most common considered to be mostly harmless.

Skin warts usually remain infected for years. Topically treatment exists but requires usually 3 to 5 treatments a day for 2 to 3 months (over 200 treatments minimum).

Skin warts of a patient were treated with 10 mg of the composition of formula A+B, three times a day for 3 days.

The warts started to soften on/after a week (7 days) and becoming white.

The skin tissue disappeared completely after 3 weeks.

Conclusion:

The composition containing the combination A-B have similar efficacy individually or combined.

Preparation of the Medication of the Composition of Formula A and Formula B (A+B)

The composition of formula A+B is a clear liquid, which preferably is mixed with a base oil such as Olive or *Macadamia* oil, preferably at a rate of 45 wt. % of A, 5 wt. % of B and 50 wt. % of base oil.

In vivo Antiviral Activity of the Composition of Formula A+B

Example 3

RNA-Enveloped Viruses: PRRS

PRRS—Porcine Reproductive and Respiratory Syndrome—is a major cause of disease in pigs; it is present in virtually all pig herds with 100% of adults being sero-positive. The disease is characterized by abortion and stillbirths in adults and respiratory disease, diarrhea and poor growth characteristics in piglets.

Two PRRS confirmed piglets were treated immediately with 500 mg of the composition of formula A+B, three times a day for 4 days. The piglets, which were very week at the start of the treatment and would recover at best after 7-10 days, showed signs of recovery on/after one day of treatment.

The piglets were confirmed PRRS free on/after the 2nd day of treatment.

The piglets recovered completely after 4 days.

Example 4

RNA-Non-Enveloped Viruses: Rota Virus 3 piglets with confirmed Rotavirus infections were treated immediately with 500 mg of the compound of formula A+B, three times a day for 2 days. All 3 piglets, which would normally experience 3 to 4 days of severe symptoms including diarrhea stopped having diarrhea after one day.

The de-activation of the Rota virus infected was confirmed on/after the second day.

The piglets recovered completely within 2 days.

Conclusion:

The efficacy of the composition containing the compounds of formula A+B is similar to the efficacy of compound A and compound B tested individually.

Preparation of the Medical composition and Examples of efficacy

Composition Containing the Combination of Compounds of Formula B and Formula C (B+C)

Preparation of the Medication of the Combination of Formula B+C

The composition of formula B+C is a clear liquid, which preferably is mixed with a base oil such as Olive or *Macadamia* oil, preferably at a rate of 5 wt. % of B and 15 wt. % of C and 80 wt. % of a base oil.

In vivo Antiviral Activity of the Composition of Formula B+C

Example 1

DNA-Enveloped Viruses: Herpes Labialis

Herpes labialis is a common disease caused by infection of the mouth area with herpes simplex virus type 1. Most people are infected with this virus by the age of 20 years. An outbreak usually involves skin lesions or rash around the lips, mouth and gums. Untreated, the symptoms will generally go away in 1 to 2 weeks.

One confirmed Herpes Labialis patient who traditionally had Herpes severe lesions that lasted two weeks was treated topically immediately on the onset of the lesions with 10 mg of the compound of formula B+C, three times a day for 1 day.

The infection did not get worse and the lesions started to disappear on/after the second day.

The patient had no more signs of infection after the 4th day.

Example 2

DNA-Non-Enveloped Viruses: Papilloma Virus

A wart is generally a small, rough growth, typically on a human's hands or feet but often other locations, that can resemble a cauliflower or a solid blister. They are caused by a viral infection, specifically by human papilloma virus 2 and 7. There are more than 10 varieties of warts, the most common considered to be mostly harmless.

Skin warts usually remain infected for years. Topically treatment exists but requires usually 3 to 5 treatments a day for 2 to 3 months (over 200 treatments minimum). Skin warts of a patient were treated with 10 mg of the compound of formula B+C, three times a day for 3 days.

The warts started to soften after a week (7 days) and becoming white.

The skin tissue disappeared completely after 3 weeks (21 days).

Conclusion:

The efficacy of the composition containing the compounds of formula B+C is similar to the efficacy of compound B and compound C tested individually.

Composition Containing the Combination of Compounds of Formula B and Formula C (B+C)

The composition containing the compounds of formula B+C is a clear liquid, which preferably is mixed with a base oil such as Olive or *Macadamia* oil, preferably at a rate of 10 wt. % of B and 40 wt. % of C and 50 wt. % of a base oil.

In vivo Antiviral Activity of the Composition of Formula B+C

Example 3

RNA-Enveloped Viruses: PRRS

PRRS—Porcine Reproductive and Respiratory Syndrome—is a major cause of disease in pigs; it is present in virtually all pig herds with 100% of adults being sero-positive. The disease is characterized by abortion and stillbirths in adults and respiratory disease, diarrhea and poor growth characteristics in piglets.

Two PRRS confirmed piglets were treated immediately with 500 mg of the compound of formula B+C, three times a day for 4 days. The piglets, which were very week at the start of the treatment and would recover at best after 7-10 days, showed signs of recovery on/after one day of treatment.

The piglets were confirmed PRRS free on/after the $2^{nd}$ day of treatment.

The piglets recovered completely after 4 days.

Example 4

RNA-Non-Enveloped Viruses: Rota Virus 3 piglets with confirmed Rotavirus infections were treated immediately with 500 mg of the compounds of formula B+C, three times a day for 2 days. All 3 piglets, which would normally experience 3 to 4 days of severe symptoms including diarrhea stopped having diarrhea on/after one day.

The de-activation of the Rota virus infected was confirmed on/after the second day.

The piglets recovered completely within 2 days.

Conclusion:

The efficacy of the composition containing the compounds of formula B+C is similar to the efficacy of compound B and compound C tested individually.

Composition Containing the Combination of Compounds of Formula A and Formula C (A+C)

Preparation of the Medication

The composition containing the combination of formula A+C is a clear liquid, composed of 25 wt. % of compound A and 25 wt. % of compound C which preferably is mixed with a base oil such as Olive or *Macadamia* oil, preferably at a rate of 50 wt. % of a base oil.

In vivo Antiviral Activity of the Composition of Formula A+C

Example 1

DNA-Enveloped Viruses: Canine Herpes

Canine Herpes virus is a leading case of puppy deaths. It lives in the respiratory and reproductive tracts of adult dogs, which show no symptoms. It is transferred to puppies during birth or via airborne nasal secretions once born. It is very contagious and spreads rapidly through litters, causing liver damage, hemorrhages, blindness and staggering. Death occurs within 24-48 hours. There is no conventional cure and treatment aimed at supportive care. Vaccination does not exist.

One confirmed Canine Herpes infected puppy was treated immediately with 300 mg of the composition of formula A+C, three times a day for 4 days. The puppy, which under normal circumstances would have died, showed signs of recovery on/after the second day of treatment.

The puppy was confirmed Herpes free on/after the $4^{th}$ day of treatment.

The puppy recovered completely after 10 days.

Example 2

DNA-Non-Enveloped Viruses: Parvo Virus

Parvovirus is a highly contagious disease and major killer of puppies. It is characterized by bloody diarrhea and progresses rapidly, with death occurring often within two days. It is transmitted via infected faeces.

A puppy from a nest of confirmed Parvo infected puppies was treated immediately with 300 mg of the compound of formula A+C, three times a day for 4 days. The puppy, which under normal circumstances would have died, showed signs of recovery on/after the first day of treatment.

The puppy was confirmed Parvo free on/after the $4^{th}$ day of treatment.

The puppy recovered completely after 6 days.

Example 3

RNA-Enveloped Viruses: PRRS

PRRS—Porcine Reproductive and Respiratory Syndrome—is a major cause of disease in pigs; it is present in virtually all pig herds with 100% of adults being sero-positive. The disease is characterized by abortion and stillbirths in adults and respiratory disease, diarrhea and poor growth characteristics in piglets Two PRRS confirmed piglets were treated immediately with 500 mg of the compound of formula A+C, three times a day for 4 days. The piglets, which were very week at the start of the treatment and would recover at best after 7-10 days, showed signs of recovery on/after one day of treatment.

The puppies were confirmed PRRS free on/after the $2^{nd}$ day of treatment.

The puppies recovered completely after 4 days.

Example 4

RNA-Non-Enveloped Viruses: Rota Virus

Three piglets with confirmed Rotavirus infections were treated immediately with 500 mg of the compound of formula A+C, three times a day for 2 days. All 3 piglets, which would normally experience 3 to 4 days of severe symptoms including diarrhea stopped having diarrhea on/after one day.

The de-activation of the Rota virus infected was confirmed on/after the first day.

The piglets recovered completely within 2 days.

Conclusion:

The efficacy of the composition containing the compounds of formula A+C is similar to the efficacy of compound A and compound C tested individually.

Preparation of the Medical composition and Examples of efficacy

Composition Containing the Combination of Compounds of Formula A and Formula B and Formula C (A+B+C)

Preparation of the Medication of the Composition:

The composition of formula A+B+C is a clear liquid, which preferably is mixed with a base oil such as Olive or *Macadamia* oil, preferably at a rate of 21 wt. % (A=7 wt. %, B=7 wt. %,C=7 wt. %) and 79 wt. % of a base oil.

In vivo Antiviral Activity of the Composition of Formula A+B+C

Example 1

DNA-Enveloped Viruses: Herpes Labialis

Herpes labialis is a common disease caused by infection of the mouth area with herpes simplex virus type 1. Most people are infected with this virus by the age of 20. An outbreak usually involves skin lesions or rash around the lips, mouth, and gums. Untreated, the symptoms will generally go away in 1 to 2 weeks.

One confirmed Herpes Labialis patient who traditionally had Herpes severe lesions that lasted two weeks was treated topically immediately on the onset of the lesions with 10 mg of the compound of formula A+B+C, three times a day for 1 day. The infection did not get worse and the lesions started to disappear on/after the second day.

The patient had no more signs of infection after the $4^{th}$ day.

Example 2

DNA-Non-Enveloped Viruses: Papilloma Virus

A wart is generally a small, rough growth, typically on a human's hands or feet but often other locations, that can resemble a cauliflower or a solid blister. They are caused by a viral infection, specifically by human papilloma virus 2 and 7. There are more than 10 varieties of warts, the most common considered to be mostly harmless.

Skin warts usually remain infected for years. Topically treatment exists but requires usually 3 to 5 treatments a day for 2 to 3 months (over 200 treatments minimum).

Skin warts of a patient were treated with 10 mg of the compound of formula A+B+C, three times a day for 3 days.

The warts started to soften on/after a week (7 days) and becoming white.

The skin tissue disappeared completely after 3 weeks (21 days).

Conclusion:

The composition containing the combination of the compounds of formula A+B+C has similar efficacy than the compound of formula A or B or C tested individually.

Preparation of the Medication of the Composition A+B+C:

The composition of formula A+B+C is a clear liquid, which preferably is mixed with a base oil such as Olive or *Macadamia* oil, preferably at a rate of 20 wt. % of A, 10 wt. % of B, 20 wt. % of C and 50 wt. % of a base oil.

In vivo Antiviral Activity of the Composition of Formula A+B+C

Example 3

RNA-Enveloped Viruses: PRRS

PRRS—Porcine Reproductive and Respiratory Syndrome—is a major cause of disease in pigs; it is present in virtually all pig herds with 100% of adults being sero-positive. The disease is characterized by abortion and stillbirths in adults and respiratory disease, diarrhea and poor growth characteristics in piglets.

Two PRRS confirmed piglets were treated immediately with 500 mg of the compound of formula A+B+C, three times a day for 4 days. The piglets, which were very week at the start of the treatment and would recover at best after 7-10 days, showed signs of recovery on/after one day of treatment.

The piglets were confirmed PRRS free on/after the $2^{nd}$ day of treatment.

The piglets recovered completely after 4 days.

Example 4

RNA-Non-Enveloped Viruses: Rota Virus

Three piglets with confirmed Rotavirus infections were treated immediately with 500 mg of the compound of formula A+B+C, three times a day for 2 days. All 3 piglets, which would normally experience 3 to 4 days of severe symptoms including diarrhea stopped having diarrhea after one day.

The de-activation of the Rota virus infected was confirmed on/after the first day.

The piglets recovered completely within 2 days.

Conclusion:

The composition containing the combination of the compounds of formula A+B+C has similar efficacy than the compound of formula A or B or C tested individually.

TABLE 1

Summary of the results:

| Composition containing compound(s) of Formula | Virus group | Virus type | Subject | Dose | Times/ day | Days | Untreated - Improvement Standard in days | Treated - Improvement (in days) | Untreated - Standard Recovery (in days) | Treated Virus or symptom free |
|---|---|---|---|---|---|---|---|---|---|---|
| A | DNA envelopped | Canine Herpes | Dog (puppy) | 300 mg | 3 | 4 | None | 2 | death | Day 4 |
| A | DNA non envelopped | Parvo | Dog (puppy) | 300 mg | 3 | 4 | None | 1 | death | Day 4 |
| A | RNA envelopped | PRRS | Pig (piglet) | 500 mg | 3 | 4 | 3-4 | 1 | 7-10 days | Day 2 |
| A | RNA non envelopped | Rota | Pig (piglet) | 500 mg | 3 | 2 | 3-4 | 1 | 4-5 days | Day 2 |

TABLE 1-continued

| Summary of the results: | | | | | | | | | | |
|---|---|---|---|---|---|---|---|---|---|---|
| Composition containing compound(s) of Formula | Virus group | Virus type | Subject | Dose | Times/ day | Days | Untreated - Improvement Standard in days | Treated - Improvement (in days) | Untreated - Standard Recovery (in days) | Treated Virus or symptom free |
| B | DNA enveloped | Herpes | Human (skin) | 10 mg | 3 | 1 | 5-7 | 3 | 7-14 days | Day 4 |
| B | DNA non enveloped | HPV | Human (skin) | 10 mg | 3 | 3 | years | 7 | years | 21 days |
| B | RNA enveloped | PRRS | Pig (piglet) | 50 mg | 6 | 3 | 3-4 | 2 | 7-10 days | Day 3 |
| B | RNA non enveloped | Rota | Pig (piglet) | 50 mg | 6 | 2 | 3-4 | 2 | 4-5 days | Day 3 |
| C | DNA enveloped | Canine Herpes | Dog (puppy) | 300 mg | 3 | 4 | None | 2 | Death | Day 4 |
| C | DNA non enveloped | Parvo | Dog (puppy) | 300 mg | 3 | 4 | None | 1 | Death | Day 4 |
| C | RNA enveloped | PRRS | Pig (piglet) | 500 mg | 3 | 4 | 3-4 | 1 | 7-10 days | Day 2 |
| C | RNA non enveloped | Rota | Pig (piglet) | 500 mg | 3 | 2 | 3-4 | 1 | 4-5 days | Day 2 |
| A + C | RNA non enveloped | Rota | Pig (piglet) | 500 mg | 3 | 2 | 3-4 | 1 | 7-10 days | Day 2 |
| A + C | DNA non enveloped | Parvo | Dog (puppy) | 300 mg | 3 | 4 | No | 1 | death | Day 4 |
| A + C | RNA enveloped | PRRS | Pig (piglet) | 500 mg | 3 | 4 | 3-4 | 1 | 7-10 days | Day 2 |
| A + C | DNA enveloped | Canine Herpes | Dog (puppy) | 300 mg | 3 | 4 | None | 2 | death | Day 4 |
| A + B | DNA enveloped | Herpes | Human (skin) | 10 mg | 3 | 1 | 5-7 | 3 | 7-14 days | Day 4 |
| A + B | DNA non enveloped | HPV | Human (skin) | 10 mg | 3 | 3 | years | 7 | years | 21 days |
| A + B | RNA enveloped | PRRS | Pig (piglet) | 500 mg | 3 | 4 | 3-4 | 1 | 7-10 days | Day 2 |
| A + B | RNA non enveloped | Rota | Pig (piglet) | 500 mg | 3 | 2 | 3-4 | 1 | 4-5 days | Day 2 |
| B + C | DNA enveloped | Herpes | Human (skin) | 10 mg | 3 | 1 | 5-7 | 3 | 7-14 days | Day 4 |
| B + C | DNA non enveloped | HPV | Human (skin) | 10 mg | 3 | 3 | years | 7 | years | 21 days |
| B + C | RNA enveloped | PRRS | Pig (piglet) | 500 mg | 3 | 4 | 3-4 | 1 | 7-10 days | Day 2 |
| B + C | RNA non enveloped | Rota | Pig (piglet) | 500 mg | 3 | 2 | 3-4 | 1 | 3-4 days | Day 2 |
| A + B + C | DNA non enveloped | HPV | Human (skin) | 10 mg | 3 | 3 | Years | 7 | years | 21 days |
| A + B + C | DNA enveloped | Herpes | Human (skin) | 10 mg | 3 | 1 | 5-7 | 3 | 7-10 days | Day 4 |
| A + B + C | RNA enveloped | PRRS | Pig (piglet) | 500 mg | 3 | 4 | 3-4 | 1 | 7-10 days | Day 2 |
| A + B + C | RNA non enveloped | Rota | Pig (piglet) | 500 mg | 3 | 2 | 3-4 | 1 | 4-5 days | Day 2 |

TABLE 2

| composition per wt. % per virus type | | | | | | | | | | | | | | | | | | |
|---|---|---|---|---|---|---|---|---|---|---|---|---|---|---|---|---|---|---|
| Composition containing | Canine Herpes | | | Parvo Virus | | | PRRS | | | Rota Virus | | | HSV | | | HPV | | |
| compound(s) of Formula | A wt. % | B wt. % | C wt. % | A wt. % | B wt. % | C wt. % | A wt. % | B wt. % | C wt. % | A wt. % | B wt. % | C wt. % | A wt. % | B wt. % | C wt. % | A wt. % | B wt. % | C wt. % |
| A | 50 | | | 50 | | | 50 | | | 50 | | | | | | | | |
| B | | | | | | | | 10 | | | 10 | | | 20 | | | 20 | |
| C | | | 50 | | | 50 | | | 50 | | | 50 | | | | | | |
| A + B | | | | | | | 45 | 5 | | 45 | 5 | | 10 | 10 | | 10 | 10 | |
| B + C | | | | | | | | 5 | 45 | | 5 | 45 | | 5 | 15 | | 5 | 15 |
| A + C | 25 | | 25 | 25 | | 25 | 25 | | 25 | 25 | | 25 | | | | | | |
| A + B + C | | | | | | | 20 | 10 | 20 | 20 | 10 | 20 | 7 | 7 | 7 | 7 | 7 | 7 |

The same results are achieved with 100 wt. % of compounds of formula A, B or C.

The invention claimed is:

1. A compound having a structure according to any one of Formula A, Formula B, or Formula C Formula A

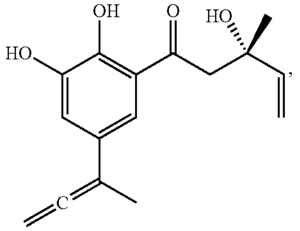

Formula B

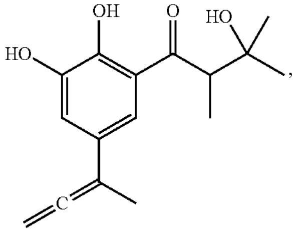

or

Formula C

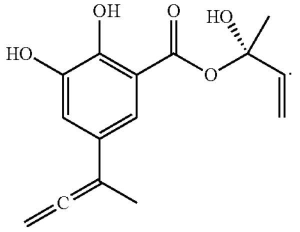

2. The compound of claim 1, having a structure according to Formula A.

3. The compound of claim 1, having a structure according to Formula B.

4. The compound of claim 1, having a structure according to Formula C.

5. A pharmaceutical composition comprising:

a carrier; and a compound having a structure according to Formula A, Formula B, or Formula C, Formula A

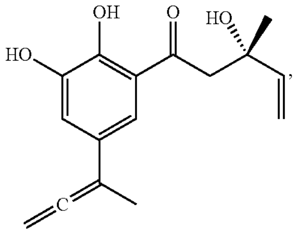

Formula B

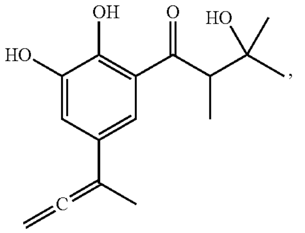

or

-continued

Formula C

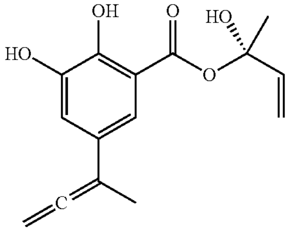

wherein the compound is present in an amount effective to reduce a viral load of at least one of herpes labialis, human papillomavirus, parvovirus, Porcine Reproductive and Respiratory Syndrome (PRRS) virus, and rotavirus in a mammal when administered to the mammal.

6. The pharmaceutical composition of claim 5 wherein the compound has a structure according to Formula A.

7. The pharmaceutical composition of claim 5 wherein the compound has a structure according to Formula B.

8. The pharmaceutical composition of claim 5 wherein the compound has a structure according to Formula C.

9. The pharmaceutical composition of claim 5 wherein the amount of the compound is at least 0.1 mg per dosage unit.

10. The pharmaceutical composition of claim 5 wherein the amount of the compound per dosage unit is between 0.1 mg and 5000 mg, inclusive.

11. The pharmaceutical composition of claim 5 wherein the carrier comprises olive oil or macadamia oil.

12. The pharmaceutical composition of claim 5 wherein the pharmaceutical composition is formulated for at least one of oral administration, topical administration, and administration via a patch.

13. The pharmaceutical composition of claim 5 wherein the pharmaceutical composition is formulated for administration by at least one of injection and infusion.

14. A method of treating a mammal for at least one of herpes labialis, papillomavirus, parvovirus, PRRS, and rotavirus comprising:

providing a pharmaceutical composition comprising a compound having a structure according to Formula A, Formula B, or Formula C, Formula A

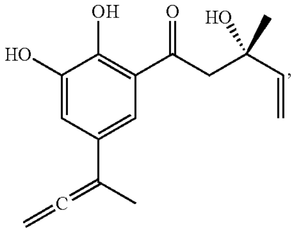

Formula B

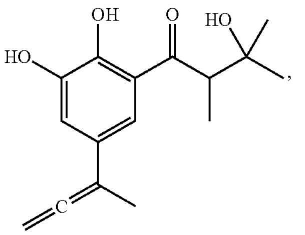

or

-continued

Formula C

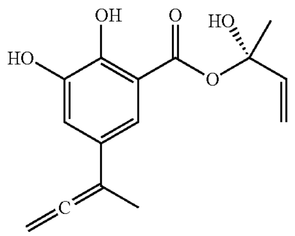

wherein the compound is present in the pharmaceutical composition in an amount effective to treat the at least one of herpes labialis, papillomavirus, parvovirus, Porcine Reproductive and Respiratory Syndrome (PRRS) virus, and rotavirus when administered to a human in need thereof; and administering the pharmaceutical composition to the human under a protocol effective to treat the at least one of herpes labialis, papillomavirus, parvovirus, PRRS, and rotavirus.

15. The method of claim 14 wherein the step of administering the pharmaceutical composition is performed at least once per day.

16. The method of claim 14 wherein the protocol comprises applying the pharmaceutical composition to a lesion or a rash on the human's skin affected by the at least one of herpes labialis, human papillomavirus parvovirus, Porcine Reproductive and Respiratory Syndrome (PRRS) virus, and rotavirus.

17. A method of reducing the incidence of infection of a human with at least one of herpes labialis, human papillomavirus, parvovirus, Porcine Reproductive and Respiratory Syndrome (PRRS) virus, and rotavirus comprising:

providing a pharmaceutical composition comprising a compound having a structure according to Formula A, Formula B, or Formula C, Formula A

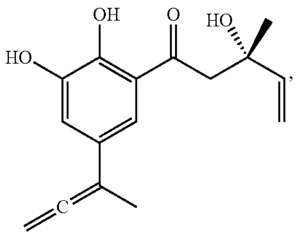,

Formula B

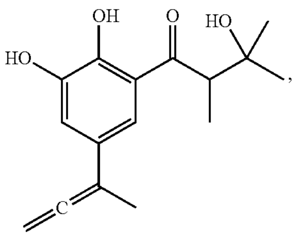, or

-continued

Formula C

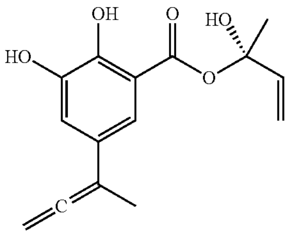

wherein the compound is present in an amount effective to reduce the likelihood that the at least one of herpes labialis, human papillomavirus, parvovirus, Porcine Reproductive and Respiratory Syndrome (PRRS) virus, and rotavirus will infect the human; and administering the pharmaceutical composition to the human using a protocol effective to reduce the likelihood that the at least one of herpes labialis, human papillomavirus, parvovirus, Porcine Reproductive and Respiratory Syndrome (PRRS) virus, and rotavirus will infect the human.

18. A method of disinfecting a non-human surface comprising:

providing a disinfectant composition comprising at least one of Formula A, Formula B, and Formula C;

Formula A

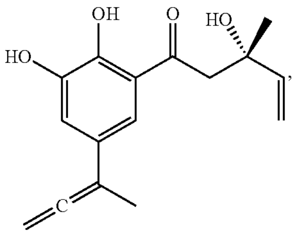,

Formula B

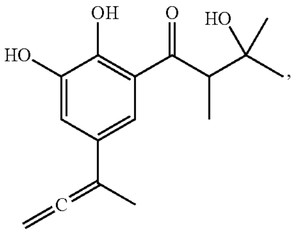, or

Formula C

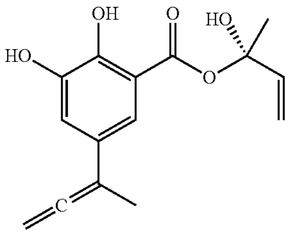

applying the disinfectant composition under a protocol effective to deactivate the at least one of herpes labialis, human papillomavirus, parvovirus, Porcine Reproductive and Respiratory Syndrome (PRRS) virus, and rotavirus.

* * * * *